United States Patent
Hansen et al.

(10) Patent No.: US 11,851,639 B2
(45) Date of Patent: *Dec. 26, 2023

(54) LIQUID CLEANING COMPOSITIONS COMPRISING PROTEASE VARIANTS

(71) Applicant: NOVOZYMES A/S, Bagsvaerd (DK)

(72) Inventors: Peter Kamp Hansen, Lejre (DK); Esben Peter Friis, Herlev (DK); Torben Vedel Borchert, Birkeroed (DK); Lars Lehmann Hylling Christensen, Alleroed (DK); Jens Erik Nielsen, Bagsvaerd (DK); Maria Berggaard Silow, Lund (SE)

(73) Assignee: NOVOZYMES A/S, Bagsvaerd (DK)

(*) Notice: Subject to any disclaimer, the term of this patent is extended or adjusted under 35 U.S.C. 154(b) by 0 days.

This patent is subject to a terminal disclaimer.

(21) Appl. No.: 17/501,781

(22) Filed: Oct. 14, 2021

(65) Prior Publication Data

US 2022/0025300 A1    Jan. 27, 2022

Related U.S. Application Data

(63) Continuation of application No. 16/282,493, filed on Feb. 22, 2019, now Pat. No. 11,174,452, which is a continuation of application No. 15/532,595, filed as application No. PCT/EP2015/078588 on Dec. 3, 2015, now Pat. No. 10,260,024.

(30) Foreign Application Priority Data

Dec. 4, 2014 (EP) ..................... 14196296
Nov. 12, 2015 (EP) ..................... 15194218

(51) Int. Cl.
  C11D 3/386 (2006.01)
  C12N 9/54 (2006.01)
  C11D 3/04 (2006.01)
  C11D 3/08 (2006.01)

(52) U.S. Cl.
  CPC .......... C11D 3/38618 (2013.01); C11D 3/044 (2013.01); C11D 3/08 (2013.01); C12N 9/54 (2013.01); C12Y 304/21062 (2013.01)

(58) Field of Classification Search
  CPC ....... C11D 3/38618; C11D 3/044; C11D 3/08; C12N 9/54; C12Y 304/21062
  See application file for complete search history.

(56) References Cited

U.S. PATENT DOCUMENTS

| 10,093,887 | B2  | 10/2018 | Aehle et al. |
| 10,260,024 | B2  | 4/2019  | Hansen et al. |
| 11,174,452 | B2* | 11/2021 | Hansen .................. C11D 3/08 |
| 2010/0192985 | A1 | 8/2010 | Aehle |
| 2013/0123162 | A1 | 5/2013 | Souter |
| 2017/0335307 | A1 | 11/2017 | Toscano |

FOREIGN PATENT DOCUMENTS

| EP | 2578679 A1 | 4/2013 |
| WO | 2009/102854 A1 | 8/2009 |
| WO | 2011/072117 A1 | 6/2011 |
| WO | 2013/004635 A1 | 1/2013 |
| WO | 2009/149144 A2 | 12/2013 |
| WO | 2014/083096 A2 | 6/2014 |
| WO | 2014/183921 A1 | 11/2014 |
| WO | 2014/207228 A1 | 12/2014 |
| WO | 2016/001449 A1 | 1/2016 |
| WO | 2016/087617 A1 | 6/2016 |
| WO | 2016/096711 A2 | 6/2016 |

OTHER PUBLICATIONS

Broun et al, 1998, Science 282, 1315-1317.
Devos et al, 2000, Proteins Struc Func Bioinf 41, 98-107.
Kisselev, 2002, Structure 10, 8-9.
Seffernick et al, 2001, J Bacteriol 183(8), 2405-2410.
Witkowski et al, 1999, Biochemistry 38, 11643-11650.
Whisstock et al, 2003, Q Rev Biophysics 36(3), 307-340.

* cited by examiner

*Primary Examiner* — Ganapathirama Raghu
(74) *Attorney, Agent, or Firm* — Kelly Reynolds

(57) ABSTRACT

The present invention relates to compositions comprising protease variants suitable for use in cleaning or detergent compositions, such as laundry detergent compositions and dish wash compositions, including automatic dish wash compositions.

20 Claims, No Drawings

Specification includes a Sequence Listing.

LIQUID CLEANING COMPOSITIONS COMPRISING PROTEASE VARIANTS

CROSS-REFERENCE TO RELATED APPLICATIONS

This application is a continuation of U.S. application Ser. No. 16/282,493 filed Feb. 22, 2019 now U.S. Pat. No. 11,174,452, issued Nov. 16, 2021, which is a continuation of U.S. application Ser. No. 15/532,595 filed Jun. 2, 2017, now U.S. Pat. No. 10,260,024 issued Apr. 16, 2019, which is a 35 U.S.C. 371 national application of PCT/EP2015/078588 filed Dec. 3, 2015 and published as WO2016/087619 on Jun. 9, 2016, which claims priority or the benefit under 35 U.S.C. 119 of European application nos. 14196296.9 and 15194218.2, filed Dec. 4, 2014, and Nov. 12, 2015, respectively, the contents of which are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions comprising protease variants suitable for use in, e.g., high pH cleaning or detergent compositions, such as laundry detergent compositions and dish wash compositions, including automatic dish wash compositions.

Description of the Related Art

In the detergent industry, enzymes have for many decades been implemented in washing formulations. Enzymes used in such formulations comprise amylases, cellulases, lipases, mannosidases, and proteases, as well as other enzymes or mixtures thereof. Commercially the most important enzymes are proteases. Many of the proteases traditionally used in cleaning processes are alkaline proteases usually having a pH optimum around 9 thus suitable for fairly alkaline detergents. However, some particular liquid detergents have a pH above 10 and these detergents have not previously been considered suitable for enzymes due to the very harsh conditions and the resulting low storage stability of enzymes in such detergents. In addition, enzymes tend to be less stable in liquid detergents in particular when the water content is high.

A number of useful protease variants have been described many of which have improved activity, stability, and solubility in different detergents However, these variants are not suitable for very high pH detergent as the alkaline environment of these detergents would make the enzymes disintegrate and thus lower their activity after a very short time.

SUMMARY OF THE INVENTION

The present invention relates to protease variants stable under alkaline conditions and suitable for use in high pH liquid cleaning and detergent compositions comprising such variants.

The present invention relates to a liquid cleaning composition having pH 10 or above, comprising at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10.

In another embodiment, the present invention relates to a liquid cleaning composition having pH 10 or above, comprising: (a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10; and (b) optionally, a protease inhibitor, preferably said protease inhibitor is a peptide aldehyde protease inhibitor.

In another embodiment, the present invention relates to a liquid cleaning composition comprising: (a) from 20% to 95% wt, preferably from 40% to 95% wt, further preferably from about 70% to about 90% wt water; (b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10; and (c) optionally, a protease inhibitor, preferably said protease inhibitor is a peptide aldehyde protease inhibitor.

The invention further relates to a liquid cleaning composition comprising:
(a) from 0% to 20% wt, preferably 0.1% to 2.5% wt of a detergent surfactant;
(b) from 40% to 95% wt, preferably from about 70% to about 90% wt water;
(c) from 1% to 30% wt of an alkaline buffer system comprising an alkali metal silicate or an alkali metal hydroxide or a mixture thereof, to provide a pH of from about 11 to 13.5; and
(d) from 0.001% to 10% wt, preferably 0.1% to 5% wt of a protease variant.

In another embodiment, the present invention further relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant; and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;
(e) optionally, a protease inhibitor, preferably said protease inhibitor is a peptide aldehyde protease inhibitor.

In said embodiment, (c1) and (c2) can be used as alternatives to each other or they can be used in combination with each other.

Definitions

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

The term "detergent component" is defined herein to mean the types of chemicals which can be used in cleaning compositions such as detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

The term "cleaning composition" includes "detergent composition" and includes, unless otherwise indicated, all forms of cleaning compositions such as bar, homogenous tablet, tablet having two or more layers, pouch having one or more compartments, regular or compact powder, gel, granulate, liquid (e.g. regular, compact or concentrated liquid), paste, powder, spray or tablet compositions including heavy-duty liquids (HDL), fine-fabric liquid detergents, liquid and/or solid laundry detergents and fine fabric detergents; hard surface cleaning formulations for, e.g., glass, wood, ceramic and metal counter tops and windows; carpet cleaners; oven cleaners; fabric fresheners; fabric softeners; textile and laundry pre-spotters, as well as dish wash detergents such as hand dishwashing agents, light duty dishwashing agents, machine dishwashing agents; all-purpose or heavy-duty washing agents, liquid, gel or paste-form all-purpose washing agents, liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. Pouches can be configured as single or multi-compartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water soluble polymer blends such as polylactide and polyvinyl alcohol (known under the Trade reference M8630 as sold by MonoSol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids: US2009/0011970 A1.

Detergent ingredients (or components) can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

The cleaning composition (e.g. liquid cleaning composition) as described herein is suitable for use in a cleaning process such as laundry or hard surface cleaning including dish wash and industrial cleaning. Exemplary laundry process may be selected from a group consisting of: residential laundry process, industrial laundry process and institutional laundry process.

In addition to containing a protease variant of the invention, the detergent formulation may contain one or more additional enzymes (such as, perhydrolases, amylases, catalases, cellulases (e.g., endoglucanases), cutinases, haloperoxygenases, lipases, mannanases, pectinases, pectin lyases, peroxidases, proteases, DNases, xanthanases, and xyloglucanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxidoreductases, bluing agents and fluorescent dyes, antioxidants, and solubilizers.

The term "dish wash" refers to all forms of washing dishes, e.g., by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics such as melamine, metals, china, glass and acrylics.

The term "dish washing composition" refers to all forms of compositions for cleaning hard surfaces. The present invention is not restricted to any particular type of dish wash composition or any particular detergent.

The term "expression" includes any step involved in the production of a variant including, but not limited to, transcription, post-transcriptional modification, translation, post-translational modification, and secretion.

The term "expression vector" means a linear or circular DNA molecule that comprises a polynucleotide encoding a variant and is operably linked to control sequences that provide for its expression.

The term "hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics such as melamine, metals, china, glass and acrylics.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "improved property" means a characteristic associated with a protease variant that is improved compared to the parent protease. Such improved properties include, but are not limited to, wash performance, protease activity, thermal activity profile, thermostability, pH activity profile, pH stability, substrate/cofactor specificity, improved surface properties, substrate specificity, product specificity, increased stability, improved stability under storage conditions, and chemical stability.

The term "stability" includes storage stability and stability during use, e.g. during a wash process and reflects the stability of the protease variant according to the invention as a function of time e.g. how much activity is retained when the protease variant is kept in solution in particular in a detergent solution. The stability is influenced by many factors e.g. pH, temperature, detergent composition e.g. amount of builder, surfactants etc. The protease stability may be measured using the assay described in example 3. The term "improved stability" or "increased stability" is defined herein as a variant protease displaying an increased stability in solutions, relative to the stability of the parent protease e.g. relative to SEQ ID NO: 2.

In a particular aspect of the invention, the improved stability is an improved stability in a liquid detergent having pH at 10 or above. The term "detergent stability" or "improved detergent stability is in particular an improved stability of the protease activity when a protease variant of the present invention is mixed into a liquid detergent formulation having pH at 10 or above, and then stored at a temperature between 15 and 50° C., e.g., 20° C., 30° C. or 40° C.

The term "improved wash performance" is defined herein as a protease variant according to the invention displaying an improved wash performance relative to the wash performance of the parent protease, e.g., by increased stain removal. The term "wash performance" includes wash performance in laundry but also, e.g., in dish wash. The wash performance may be quantified as described under the definition of "wash performance" herein.

The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

The term "laundering" relates to both household laundering and industrial laundering and means a process of treating textiles and/or fabrics with a solution containing a detergent composition of the present invention. The laundering process can for example be carried out using, e.g., a household or an industrial washing machine or can be carried out by hand.

The term "mature polypeptide" means a polypeptide in its final form following translation and any post-translational modifications, such as N-terminal processing, C-terminal truncation, glycosylation, phosphorylation, autocatalytic activation etc. In one aspect, the mature polypeptide is amino acids 1 to 269 of SEQ ID NO: 2 and 1 to 275 of SEQ ID NO: 1. It is known in the art that a host cell may produce a mixture of two of more different mature polypeptides (i.e., with a different C-terminal and/or N-terminal amino acid) expressed by the same polynucleotide.

The term "mature polypeptide coding sequence" means a polynucleotide that encodes a mature polypeptide having protease activity.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The term "parent" means a protease to which an alteration is made to produce the enzyme variants of the present invention. It will be understood that in the present context the expression "having identical amino acid sequence" relates to 100% sequence identity. In a particular embodiment the parent is a protease with at least 60% identity, such as at least 65%, at least 70%, at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, or 100% identity to a polypeptide of SEQ ID NO: 1 or 2.

The term "protease" is defined herein as an enzyme that hydrolyzes peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, California, including supplements 1-5 published in *Eur. J. Biochem.* 1223: 1-5 (1994); *Eur. J. Biochem.* 232: 1-6 (1995); *Eur. J. Biochem.* 237: 1-5 (1996); *Eur. J. Biochem.* 250: 1-6 (1997); and *Eur. J. Biochem.* 264: 610-650 (1999); respectively. The most widely used proteases in the detergent industry such as laundry and dish wash are the serine proteases or serine peptidases which is a subgroup of proteases characterised by having a serine in the active site, which forms a covalent adduct with the substrate. Further the subtilases (and the serine proteases) are characterized by having two active site amino acid residues apart from the serine, namely a histidine residue and an aspartic acid residue. Subtilase refer to a sub-group of serine protease according to Siezen et al., 1991, *Protein Engng.* 4: 719-737 and Siezen et al., 1997, *Protein Science* 6: 501-523. The subtilases may be divided into 6 sub-divisions, i.e., the Subtilisin family, the Thermitase family, the Proteinase K family, the Lantibiotic peptidase family, the Kexin family and the Pyrolysin family. The term "protease activity" means a proteolytic activity (EC 3.4). Proteases usably in detergents are mainly endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the Suc-AAPF-pNA activity assay, as described in the Materials and Methods section below. In one aspect, the protease variants of the present invention have at least 20%, e.g., at least 40%, at least 50%, at least 60%, at least 70%, at least 80%, at least 90%, at least 95%, or at least 100% of the enzyme activity of the mature polypeptide of the parent enzyme. In one particular aspect the protease variants of the present invention have at least 20%, e.g., at least 40%, at least 50%, at least 60%, at least 70%, at least 80%, at least 90%, at least 95%, or at least 100% of the enzyme activity of a polypeptide of SEQ ID NO: 2.

The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in "Materials and Methods" below. The protease variants of the present invention preferably have at least 20%, e.g., at least 40%, at least 50%, at least 60%, at least 70%, at least 80%, at least 90%, at least 95%, and at least 100% of the protease activity of a polypeptide of SEQ ID NO: 2.

The term "residual activity" means in this context the protease activity left or remaining after storage and in particular after storage in a liquid detergent. When measuring the residual activity the activity of the protease is measured at $t_1$ just after adding the protease to the detergent. The residual activity is then measured at $t_2$ after storage a certain amount of time, typical minutes or weeks. The protease variant of the invention preferably has residual activity of at least 10% at least 20%, e.g., at least 40%, at least 50%, at least 60%, at least 70%, at least 80%, at least 90%, at least 95%, or at least 100% of the protease activity before storage (at $t_1$) in a high pH liquid detergent with pH 10, at a temperature of 30° C. and when measured at t=4 hours or above. A high pH liquid detergent is in this context a liquid detergent with pH 10 or above, and a very high pH liquid detergent is in this context a liquid detergent with pH 12 or above. A protease variant according to the invention is preferably more stable i.e. has higher residual activity after storage in high pH liquid detergent (pH=10 or more) compared to the parent protease e.g. a protease with SEQ ID NO 2 and/or a protease variant according to the invention is more stable i.e. has higher residual activity after storage in liquid detergent i.e. liquid detergent comprising 40% water or above compared to the parent protease e.g. a protease with SEQ ID NO 2. Preferably the residual activity of the protease variant of the invention is at least 10%, at least 15%, at least 20%, at least 25%, at least 30%, at least 35%, at least 40%, at least 45% such as at least 50% higher compared to the residual activity of the parent protease e.g. compared to SEQ ID NO 2 when measured after storage 4 hours at 30° C. in a liquid detergent with pH 10 and/or liquid detergent with at least 40% water. As described in Example 3.

In particular, the relative stability of a protease variant according to the invention and its corresponding parent protease, are different at high pH, above or at pH 10 from their relative stabilities at neutral pH, above or at pH 7.

The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment–
Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the -nobrief option) is used as the percent identity and is calculated as follows:

(Identical Deoxyribonucleotides×100)/(Length of
Alignment–Total Number of Gaps in Alignment)

The different stringency conditions are defined as follows.

The term "substantially pure variant" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the variant is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The variants of the present invention are preferably in a substantially pure form. This can be accomplished, for example, by preparing the variant by well-known recombinant methods or by classical purification methods.

The term "substantially pure polynucleotide" means a polynucleotide preparation free of other extraneous or unwanted nucleotides and in a form suitable for use within genetically engineered polypeptide production systems. Thus, a substantially pure polynucleotide contains at most 10%, at most 8%, at most 6%, at most 5%, at most 4%, at most 3%, at most 2%, at most 1%, and at most 0.5% by weight of other polynucleotide material with which it is natively or recombinantly associated. A substantially pure polynucleotide may, however, include naturally occurring 5'- and 3'-untranslated regions, such as promoters and terminators. It is preferred that the substantially pure polynucleotide is at least 90% pure, e.g., at least 92% pure, at least 94% pure, at least 95% pure, at least 96% pure, at least 97% pure, at least 98% pure, at least 99% pure, and at least 99.5% pure by weight. The polynucleotides of the present invention are preferably in a substantially pure form.

The term "textile" means any textile material including yarns, yarn intermediates, fibers, non-woven materials, natural materials, synthetic materials, as well as fabrics made of these materials such as garments, cloths and other articles). When the term fabric or garment is used it is intended to include the broader term textiles as well.

The term "variant" means a polypeptide having protease activity comprising an alteration, i.e., a substitution, insertion, and/or deletion, at three or more (e.g., several) positions. A substitution means replacement of the amino acid occupying a position with a different amino acid; a deletion means removal of the amino acid occupying a position; and an insertion means adding one or more (e.g., several) amino acids, e.g., 1, 2, 3, 4 or 5 amino acids adjacent to and immediately following the amino acid occupying a position. The term protease variant may be a variant of a subtilase parent, i.e., a protease variant is a subtilase which comprises alterations i.e., a substitution, insertion, and/or deletion, at three or more (e.g., several) positions compared to the parent protease.

The term "wash performance" is used as an enzyme's ability to remove stains present on the object to be cleaned during, e.g., wash, such as laundry or hard surface cleaning. The improvement in the wash performance may be quantified by calculating the so-called intensity value (Int) defined in the AMSA assay.

The term "wild-type protease" means a protease expressed by a naturally occurring organism, such as a bacterium, archaea, yeast, fungus, plant or animal found in nature. An example of a wild-type subtilase is subtilisin Savinase, i.e., amino acids 1 to 269 of SEQ ID NO: 2.

Conventions for Designation of Variants

For purposes of the present invention, subtilisin BPN' (the sequence of amino acids 1-275 of SEQ ID NO: 1 (Siezen et al., 1991, *Protein Eng.* 4: 719-737)) is used to determine the corresponding amino acid residue in another protease. The amino acid sequence of another protease is aligned with the mature polypeptide disclosed in SEQ ID NO: 1, and based on the alignment, the amino acid position number corresponding to any amino acid residue in the polypeptide disclosed in SEQ ID NO: 1 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another protease can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537: 39-64; Katoh and Toh, 2010, *Bioinformatics* 26:1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 1 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions: For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively. An "X" preceding a position means that any original amino acid at the position may be substituted.

Deletions: For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions: The insertion of an additional amino acid residue such as, e.g., a lysine after G195 may be indicated by: Gly195GlyLys or G195GK. Alternatively insertion of an additional amino acid residue such as lysine after G195 may be indicated by: *195aK. When more than one amino acid residue is inserted, such as, e.g., a Lys and Ala after G195 this may be indicated as: Gly195GlyLysAla or G195GKA. In such cases, the inserted amino acid residue(s) may also be numbered by the addition of lower case letters to the position number of the amino acid residue preceding the inserted amino acid residue(s), in this example: *195aK *195bA. In the above example, the sequences 194 to 196 would thus be:

194 195 196
Subtilisin 309 A-G-L
194 195 195a 195b 196
Variant A-G-K-A-L

In cases where a substitution and an insertion occur at the same position, this may be indicated as S99SD+S99A or in short S99AD. The same modification may also be indicated as S99A+*99aD.

In cases where an amino acid residue identical to the existing amino acid residue is inserted, it is clear that degeneracy in the nomenclature arises. If for example a glycine is inserted after the glycine in the above example this would be indicated by G195GG or *195GaG. The same actual change could just as well be indicated as A194AG or *194aG for the change from:

194 195 196
Subtilisin 309 A-G-L
to:
194 195 195a 196
Variant A-G-G-L
194 194a 195 196

Such instances will be apparent to the skilled person and the indication G195GG and corresponding indications for this type of insertions are thus meant to comprise such equivalent degenerate indications.

Multiple alterations: Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively. Alternatively multiple alterations may be separated be space or a comma, e.g., A170Y G195E or A170Y, G195E respectively.

Different alterations: Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

Alternatively different alterations or optional substitutions may be indicated in brackets, e.g., Arg170[Tyr, Gly] or Arg170{Tyr, Gly} or in short R170 [Y,G] or R170 {Y, G}.

DETAILED DESCRIPTION OF THE INVENTION

Alkaline Liquid detergents having high pH are widely used in cleaning, such as laundry and dish wash cleaning. Liquid detergents with elevated pH are especially commonly used by consumers in North America. The high pH cleaning compositions are also used in industrial cleaning processes.

Alkaline detergents are liquids having detergent properties. The pH of such detergents usually ranges in pH from 9 to 12.5. The high pH detergents typically comprise components such as surfactants, builders and bleach components and additionally they may also contain a significant amount of water and alkalis such as NaOH, TSP (Trisodium phosphate), ammonia, Sodium carbonate, Potassium hydroxide (KOH) these alkalis are usually added in amount corresponding to 0.1 to 30 percent weight (wt).

Examples of commercial high pH detergents include but are not limited to Arm & Hammer (Church & Dwight), Surf Sparkling Ocean (Unilever), Clean Burst, SUN Triple Clean Tropical breeze (SUN products), Purex Free and Clear (Henkel) and Xtra Tropical Passion (Church & Dwight).

Adding enzymes to detergents are highly advantageous as the specific activities of these enzymes effectively removes specific stains from surfaces such as textile and cutlery. However, the difficulty of maintaining acceptable enzyme stability in the high pH liquid detergents has for many years prohibited inclusion of enzymes into these detergents.

The present invention relates high pH liquid cleaning compositions comprising alkaline stable protease variants suitable for use in such compositions.

One aspect of the invention relates to a liquid cleaning composition comprising:
(a) from 0% to 20% wt, preferably 0.1% to 2.5% wt of a detergent surfactant;
(b) from 40% to 95% wt, preferably from about 70% to about 90% wt water;
(c) from 1% to 30% wt of an alkaline buffer system comprising an alkali metal silicate or an alkali metal hydroxide or a mixture thereof, to provide a pH of from about 11 to 13.5; and
(d) from 0.001% to 10% wt, preferably 0.1% to 5% wt of a protease variant.

In another embodiment, the present invention relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant; and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 7.5 to 13.5, preferably the pH is from about 10 to 13.5;
(d) optionally, a protease inhibitor, preferably said protease inhibitor is a peptide aldehyde protease inhibitor.

The compositions of the invention preferably contain alkaline buffer systems to provide a pH of at least about 7.5, at least about 8, at least about 9, preferably pH 10 or above. Preferably the pH is from about 9 to about 13. In order to achieve the high pH it is necessary to have present an alkali metal hydroxide especially sodium or potassium hydroxide, normally in an amount of 0.1 to about 30% by weight (percentage by weight, abbreviated wt %) of the composition, and preferably 1.0 to 2.5%, or higher amounts of a suitable alkali metal silicate such as metal silicate, according to the desired pH for the product.

The composition of the invention preferably contain from 20% to 95% wt, preferably from 40% to 95% wt, further preferably from about 70% to about 90% wt water. Preferably from about 75 to 80% wt water, preferably from about 80 to 85% wt water, preferably from about 70-75% wt water or preferably from about 75-80% wt water. Preferably the composition of the invention comprises 10% wt or more water, such as at least 20% wt, at least 25% wt, at least 30% wt, at least 35% wt, at least 40% wt, at least 45% wt, at least 50% wt, at least 55% wt, at least 60% wt, at least 65% wt, at least 70% wt, at least 75% wt, at least 80% wt, at least 85% wt, at least 90% wt, or at least 95% wt or more but less than 100% wt percent weight (wt) water.

The protease variants may be added to a high pH cleaning composition according to the invention in an amount corresponding to 0.01-200 mg of enzyme protein per liter of wash liquor, preferably 0.05-50 mg of enzyme protein per liter of wash liquor, in particular 0.1-10 mg of enzyme protein per liter of wash liquor.

A composition for use in laundry liquid, for example, may include 0.0001%-10%, such as 0.001-7%, such as 0.1%-5% of protease variant according to the invention by weight of the composition.

A composition for use in automatic dishwash (ADW), for example, may include 0.0001%-50%, such as 0.001%-30%, such as 0.01%-20%, such as 0.5-15% of enzyme protein by weight of the composition.

The present invention relates to a liquid cleaning composition having pH 10 or above, comprising at least 0.01 wt % protease, wherein the protease is a variant of a parent protease and wherein the protease variant has an amino acid sequence which has at least 60% sequence identity to the amino acid sequence of SEQ ID NO: 2, and wherein said protease variant is characterized by having at least 10% higher residual activity than the parent protease when measured after 4 hours at 40° C. in liquid detergent with pH 10.

The protease variants added to a cleaning composition according to the invention display half-lives that are improved to an extent that it enables the storage and use of proteases in high pH (pH>10.0) liquid cleaning compositions such as detergents. In addition the protease variants display significant wash performance in high pH liquids and it therefore opens up the possibility of improving the wash performance of high pH liquid detergents and/or reducing the concentration of detergent present in these detergent formulations to achieve the same wash performance. In addition the protease variants display significant wash performance in high pH liquids and it therefore opens up the possibility of improving the wash performance of high pH liquid detergents and/or reducing the concentration of protease present in these detergent formulations to achieve the same wash performance.

One embodiment of the invention relates to a liquid cleaning composition having pH 10 or above comprising a protease wherein the protease is a variant protease having at least 60% identity with the amino acid sequence of SEQ ID NO: 1 or 2, wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO 1). In another embodiment, the invention provides a liquid cleaning composition having pH 10 or above and comprising a protease wherein the protease is a variant protease having at least 60% identity with the amino acid sequence of SEQ ID NO: 1 or 2, wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 7 to about 13 or above comprising a protease wherein the protease is a variant protease having at least 60% identity with the amino acid sequence of SEQ ID NO: 1 or 2, and wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1). In another embodiment, the invention relates to a liquid cleaning composition having pH from about 7 to about 13 or above comprising a protease wherein the protease is a variant protease having at least 60% identity with the amino acid sequence of SEQ ID NO: 1 or 2, and wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 8 to about 13 or above comprising a protease wherein the protease is a variant protease having at least 60% identity with the amino acid sequence of SEQ ID NO: 1 or 2, and wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1). In another embodiment, the invention relates to a liquid cleaning composition having pH from about 8 to about 13 or above comprising a protease wherein the protease is a variant protease having at least 60% identity with the amino acid sequence of SEQ ID NO: 1 or 2, and wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 9 to about 13 or above comprising a protease wherein the protease is a variant protease having at least 60% identity with the amino acid sequence of SEQ ID NO: 1 or 2, and wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1). In another embodiment, the invention relates to a liquid cleaning composition having pH from about 9 to about 13 or above comprising a protease wherein the protease is a variant protease having at least 60% identity with the amino acid sequence of SEQ ID NO: 1 or 2, and wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 10 to about 13 or above comprising a protease wherein the protease is a variant protease having at least 60% identity with the amino acid sequence of SEQ ID NO: 1 or 2, and wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1). In another embodiment, the invention relates to a liquid cleaning composition having pH from about 10 to about 13 or above comprising a protease wherein the protease is a variant protease having at least 60% identity with the amino acid sequence of SEQ ID NO: 1 or 2, and wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 11 to about 13 or above comprising a protease wherein the protease is a variant protease having at least 60% identity with the amino acid sequence of SEQ ID NO: 1 or 2, and wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO 1). In another embodiment, the invention relates to a liquid cleaning composition having pH from about 11 to about 13 or above comprising a protease wherein the protease is a variant protease having at least 60% identity with the amino acid sequence of SEQ ID NO: 1 or 2, and wherein said variant comprises substitutions at positions corresponding to the positions 205 and 209 of BPN' (SEQ ID NO: 1), preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1).

One embodiment of the invention relates to a liquid cleaning composition having pH from about 7 to about 13 or above comprising a protease wherein the protease is a variant protease having at least 60% identity with the amino acid sequence of SEQ ID NO: 1 or 2, and wherein said variant comprises one or more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1). In another embodiment, the invention relates to a liquid cleaning composition having pH from about 7 to about 13 or above comprising a protease wherein the protease is a variant protease having at least 60% identity with the amino acid sequence of SEQ ID NO: 1 or 2, and wherein said variant comprises substitutions corresponding to the substitutions X205I and X209W of BPN' (SEQ ID NO: 1), preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1).

One embodiment of the invention relates to a liquid cleaning composition having pH from about 8 to about 13 or above comprising a protease wherein the protease is a variant protease having at least 60% identity with the amino acid sequence of SEQ ID NO: 1 or 2, and wherein said variant comprises one or more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1). In another embodiment, the invention relates to a liquid cleaning composition having pH from about 8 to about 13 or above comprising a protease wherein the protease is a variant protease having at least 60% identity with the amino acid sequence of SEQ ID NO: 1 or 2, and wherein said variant comprises substitutions corresponding to the substitutions X205I and X209W of BPN' (SEQ ID NO: 1), preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1).

One embodiment of the invention relates to a liquid cleaning composition having pH from about 9 to about 13 or above comprising a protease wherein the protease is a variant protease having at least 60% identity with the amino acid sequence of SEQ ID NO: 1 or 2, and wherein said variant comprises one or more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1). In another embodiment, the invention relates to a liquid cleaning composition having pH from about 9 to about 13 or above comprising a protease wherein the protease is a variant protease having at least 60% identity with the amino acid sequence of SEQ ID NO: 1 or 2, and wherein said variant comprises substitutions corresponding to the substitutions X205I and X209W of BPN' (SEQ ID NO: 1), preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1).

One embodiment of the invention relates to a liquid cleaning composition having pH from about 10 to about 13 or above comprising a protease wherein the protease is a variant protease having at least 60% identity with the amino acid sequence of SEQ ID NO: 1 or 2, and wherein said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1). In another embodiment, the invention relates to a liquid cleaning composition having pH from about 10 to about 13 or above comprising a protease wherein the protease is a variant protease having at least 60% identity with the amino acid sequence of SEQ ID NO: 1 or 2, and wherein said variant comprises substitutions corresponding to the substitutions X205I and X209W of BPN' (SEQ ID NO: 1), preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1).

One embodiment of the invention relates to a liquid cleaning composition having pH from about 11 to about 13 or above comprising a protease wherein the protease is a variant protease having at least 60% identity with the amino acid sequence of SEQ ID NO: 1 or 2, and wherein said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1). In another embodiment, the invention relates to a liquid cleaning composition having pH from about 11 to about 13 or above comprising a protease wherein the protease is a variant protease having at least 60% identity with the amino acid sequence of SEQ ID NO: 1 or 2, and wherein said variant comprises substitutions corresponding to the substitutions X205I and X209W of BPN' (SEQ ID NO: 1), preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1).

In some preferred embodiments, the protease variant is selected from the group consisting of:
S9E+N43R+G61E+N76D+G115W+H120V+A194P+ Q206L+S259D+L262E;
S9E+N43R+N76D+A194P+V205I+Q206L+Y209W+ S259D+N261W+L262E;
S9E+N43R+N76D+Q182E+A194P+V205I+Q206L+ Y209W+S259D+N261W+L262E;
S9E+N43R+N76D+A194P+V205I+Q206L+Y209W+ S216V+M222S+L262E;
S9E+N43R+N76D+A194P+V205I+Q206L+S256D+ S259D+N261W+L262E;
S9E+N18S+N43R+N76D+G115W+H120V+A194P+ V205I+Q206L+S259D+L262E;
S9E+N43R+N76D+G115W+H120V+A194P+V205I+ Q206L+S259D+L262E;
S9E+N43R+N76D+A194P+V205I+Q206L+Y209W+ S259D+N261W+L262E;
S9E+N43R+N76D+A194P+V205I+Q206L+S256D+ S259D+N261W+L262E;
S9E+N43R+N76D+Q182E+A194P+V205I+Q206L+ Y209W+S256D+S259D+N261W+L262E;
S9E+N43R+N76D+S188E+A194P+V205I+Q206L+ Y209W+S216V+L262E;
S9E+N76D+G115W+G160P+Q182E+V205I+Q206L+ Y209W+S256D+T260E+N261W+L262E;
S9E+N43R+N76D+H120T+A194P+Q206L+S256D+ S259D+N261W+L262E;
S9E+N43R+N76D+H120T+A194P+V205I+Q206L+ Y209W+S216V+L262E;
S9E+N76D+G160P+Q182E+V205I+Q206L+Y209W+ S256D+N261W+L262E;
S9E+N43R+N76D+Q182E+A194P+V205I+Q206L+ S259D+N261W+L262E;
S9E+N76D+Q182E+V205I+Q206L+Y209W+S256D+ N261W+L262E;
S9E+N43R+N76D+Q182E+A194P+V205I+Q206L+ S259D+N261W+L262E+*275aH;
S9E+N43R+N76D+Q182E+N185E+S188E+A194P+ Q206L+Y209W+S259D+L262E;
S9E+N43R+N76D+N185E+A194P+V205I+Q206L+ Y209W+S216V+L262E;
S9E+N43R+N76D+A194P+V205I+Q206L+Y209W+ S216V+N261M+L262E;
S9E+N43R+I72A+N76D+A194P+Q206L+S259D+ L262E;
S9E+N43R+N76D+A194P+V205I+Q206L+S259D+ L262E;
S9E+N43R+N76D+H120V+Q182E+A194P+V205I+ Q206L+Y209W+S256D+S259D+N261W+L262E;
S9E+N43R+N76D+A194P+V205I+Q206L+Y209W+ S259D+N261W+L262E;
S9E+N43R+N76D+V205I+Q206L+Y209W+S259D+ N261W+L262E;
S9E+N43R+N76D+Q182E+A194P+V205I+Q206L+ Y209W+S256D+S259D+N261W+L262E;
S9E+N43R+N76D+H120V+Q182E+A194P+V205I+ Q206L+Y209W+S256D+N261W+L262E+*275aH+ *275bH;
S3V+N76D+H120V+Q182E+N185E+S188E+V205I+ Q206L+Y209W+S216V+S256D+N261W+L262E;

S9E+N43R+N76D+A158E+A194P+N204D+V205I+
Q206L+Y209W+S212G+S216V+L262E;
S9E+N43R+N76D+A158E+G160P+V205I+Q206L+
Y209W+S259D+N261W+L262E;
S9E+N43R+N76D+A158E+G160P+A194P+N204D+
V205I+Q206L+Y209W+S212G+S216V+L262E;
S9E+N43R+N76D+A158E+G160P+S161E+A194P+
N204D+V205I+Q206L+Y209W+S216V+L262E+
*275aH+*275bH;
S9E+N43R+N76D+A158E+G160P+S161E+A194P+
N204D+V205I+Q206L+Y209W+L262E;
S9E+N43R+N76D+A158E+G160P+S161E+A194P+
N204D+V205I+Q206L+Y209W+S212G+S216V+
L262E+*275aH+*275bH;
S9E+N43R+N76D+A158E+G160P+S161E+A194P+
N204D+V205I+Q206L+Y209W+S212G+L262E;
S9E+N43R+N76D+A158E+A194P+V205I+Q206L+
Y209W+S259D+N261W+L262E;
S9E+N43R+N76D+A158E+G160P+S161E+A194P+
N204D+V205I+Q206L+Y209W+S212G+L262E+
*275aH+*275bH;
S9E+N43R+N76D+A158E+G160P+S161E+A194P+
N204D+V205I+Q206L+Y209W+S216V+L262E;
S9E+N43R+N76D+A158E+G160P+S161E+A194P+
Q206L+Y209W+S259D+L262E+*275aH+*275bH;
S9E+N43R+N76D+A158E+G160P+S161E+A194P+
V205I+Q206L+Y209W+S212G+S216V+L262E;
S9E+N43R+N76D+A158E+S161E+V205I+Q206L+
Y209W+S259D+N261W+L262E;
S9E+N43R+N76D+A158E+G160P+S161E+V205I+
Q206L+Y209W+S259D+N261W+L262E;
S9E+N43R+N76D+A158E+S161E+A194P+N204D+
V205I+Q206L+Y209W+S212G+S216V+L262E;
S9E+N43R+N76D+G160P+V205I+Q206L+Y209W+
S259D+N261W+L262E;
S9E+N43R+N76D+A194P+N204D+V205I+Q206L+
Y209W+S212G+S216V+S259D+N261W+L262E;
S9E+N43R+N76D+A194P+Q206L+Y209W+L262E;
S9E+N43R+N76D+A194P+Q206L+Y209W+S256D+
S259D+N261W+L262E;
S9E+N43R+N76D+A194P+Q206L+Y209W+T255E+
S256D+S259D+T260E+N261W+L262E;
S9E+N43R+N76D+V205I+Q206L+Y209W+S259D+
N261W+L262E;
S9E+N43R+N76D+G115W+H120V+A194P+Q206L+
Y209W+S259D+L262E;
S9E+N43R+N76D+G115W+H120V+P129D+A194P+
Q206L+Y209W+S259D+L262E;
S9E+N43R+N76D+G160P+A194P+N204D+V205I+
Q206L+Y209W+S212G+S216V+L262E;
S9E+N43R+N76D+G160P+S161E+A194P+N204D+
V205I+Q206L+Y209W+S212G+S216V+L262E;
S9E+N43R+N76D+G160P+S161E+A194P+N204D+
V205I+Q206L+Y209W+S212G+S216V+L262E+*275aH+
*275bH;
S9E+N43R+N76D+N204D+V205I+Q206L+Y209W+
S259D+N261W+L262E;
S9E+N43R+N76D+G160P+S161E+V205I+Q206L+
Y209W+S259D+N261W+L262E;
S9E+N43R+N76D+H120V+Q182E+A194P+V205I+
Q206L+Y209W+S256D+N261W+L262E+*275aH+
*275bH;
S9E+N43R+N76D+V205I+Q206L+Y209W+S216V+
S259D+N261W+L262E;
S9E+N43R+N76D+S161E+V205I+Q206L+Y209W+
S259D+N261W+L262E;
S9E+N43R+N76D+P131*+A194P+Q206L+Y209W+
S259D+L262E;
S9E+N43R+N76D+H120V+Q182E+A194P+V205I+
Q206L+Y209W+S256D+N261W+L262E+*275aH+
*275bH;
S9E+N43R+N76D+S161E+A194P+N204D+V205I+
Q206L+Y209W+S212G+S216V+L262E+*275aH+
*275bH;
S9E+N43R+N76D+V205I+Q206L+Y209W+S212G+
S259D+N261W+L262E;
S9E+N43R+N76D+N204D+V205I+Q206L+Y209W+
S212G+S216V+S259D+N261W+L262E.

In some preferred embodiments, the cleaning compositions provided herein are formulated such that it has a pH of from about 7.5 to about 13.5, about 8.0 to about 13.5, about 8.5 to about 13.5, about 9.0 to about 13.5, or in alternative embodiments, even from about 9.5 to about 13.5, such as from about 10 to about 13.5, from about 10 to about 13, from about 10 to about 12.5, from about 10 to about 12, from about 10 to about 11.5, from about 10 to about 11, from about 10 to about 10.5. In some preferred embodiments, the liquid cleaning composition is formulated such that pH is from about 10 to about 13.5. In other preferred embodiments, the liquid cleaning composition is formulated such that pH is from about 12 to 13.5.

One aspect of the invention relates to a liquid cleaning composition comprising:
(a) from 0% to 20% wt, preferably 0.1% to 2.5% wt of a detergent surfactant;
(b) from 40% to 95% wt, preferably from about 70% to about 90% wt water;
(c) from 1% to 30% wt of an alkaline buffer system comprising an alkali metal silicate or an alkali metal hydroxide or a mixture thereof, to provide a pH of from about 11 to 13.5; and
(d) from 0.001% to 10% wt, preferably 0.1% to 5% wt of a protease variant, wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1).

Another aspect of the invention relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant, wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1); and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 8 to 13.5, preferably the pH is from about 10 to 13.5;
(d) optionally, a protease inhibitor, preferably said protease inhibitor is a peptide aldehyde protease inhibitor.

In a preferred embodiment, the protease variant comprises the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D. Thus, one embodiment of the invention relates to a liquid cleaning composition comprising:
- (a) from 0% to 20% wt, preferably 0.1% to 2.5% wt of a detergent surfactant;
- (b) from 40% to 95% wt, preferably from about 70% to about 90% wt water;
- (c) from 1% to 30% wt of an alkaline buffer system comprising an alkali metal silicate or an alkali metal hydroxide or a mixture thereof, to provide a pH of from about 11 to 13.5; and
- (d) from 0.001% to 10% wt, preferably 0.1% to 5% wt of a protease variant, wherein said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO 1), preferably said variant comprises substitutions corresponding to the substitutions X205I and X209W of BPN' (SEQ ID NO 1), further preferably said variant comprises substitutions corresponding to the substitutions X205I and X209W of BPN' (SEQ ID NO 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO 1).

Another embodiment of the invention relates to a liquid cleaning composition comprising:
- (a) from 0% to 20% wt, preferably 0.1% to 2.5% wt of a detergent surfactant;
- (b) from 0.001% to 10% wt, preferably 0.1% to 5% wt of a protease variant, wherein said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1), preferably said variant comprises substitutions corresponding to the substitutions X205I and X209W of BPN' (SEQ ID NO: 1), further preferably said variant comprises substitutions corresponding to the substitutions X205I and X209W of BPN' (SEQ ID NO: 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO: 1); and
- (c1) from 20% to 95% wt, preferably from 40% to 95% wt, further preferably from about 70% to about 90% wt water; and/or
- (c2) from 1% to 30% wt of an alkaline buffer system comprising an alkali metal silicate or an alkali metal hydroxide or a mixture thereof, to provide a pH of from about 8 to 13.5, preferably the pH is from about 10 to 13.5;
- (d) optionally, a protease inhibitor, preferably said protease inhibitor is a peptide aldehyde protease inhibitor.

In some preferred embodiments, the protease variant is selected from the group consisting of:
- S9E+N43R+G61E+N76D+G115W+H120V+A194P+ Q206L+S259D+L262E;
- S9E+N43R+N76D+A194P+V205I+Q206L+Y209W+ S259D+N261W+L262E;
- S9E+N43R+N76D+Q182E+A194P+V205I+Q206L+ Y209W+S259D+N261W+L262E;
- S9E+N43R+N76D+A194P+V205I+Q206L+Y209W+ S216V+M222S+L262E;
- S9E+N43R+N76D+A194P+V205I+Q206L+S256D+ S259D+N261W+L262E;
- S9E+N18S+N43R+N76D+G115W+H120V+A194P+ V205I+Q206L+S259D+L262E;
- S9E+N43R+N76D+G115W+H120V+A194P+V205I+ Q206L+S259D+L262E;
- S9E+N43R+N76D+A194P+V205I+Q206L+Y209W+ S259D+N261W+L262E;
- S9E+N43R+N76D+A194P+V205I+Q206L+S256D+ S259D+N261W+L262E;
- S9E+N43R+N76D+Q182E+A194P+V205I+Q206L+ Y209W+S256D+S259D+N261W+L262E;
- S9E+N43R+N76D+S188E+A194P+V205I+Q206L+ Y209W+S216V+L262E;
- S9E+N76D+G115W+G160P+Q182E+V205I+Q206L+ Y209W+S256D+T260E+N261W+L262E;
- S9E+N43R+N76D+H120T+A194P+Q206L+S256D+ S259D+N261W+L262E;
- S9E+N43R+N76D+H120T+A194P+V205I+Q206L+ Y209W+S216V+L262E;
- S9E+N76D+G160P+Q182E+V205I+Q206L+Y209W+ S256D+N261W+L262E;
- S9E+N43R+N76D+Q182E+A194P+V205I+Q206L+ S259D+N261W+L262E;
- S9E+N76D+Q182E+V205I+Q206L+Y209W+S256D+ N261W+L262E;
- S9E+N43R+N76D+Q182E+A194P+V205I+Q206L+ S259D+N261W+L262E+*275aH;
- S9E+N43R+N76D+Q182E+N185E+S188E+A194P+ Q206L+Y209W+S259D+L262E;
- S9E+N43R+N76D+N185E+A194P+V205I+Q206L+ Y209W+S216V+L262E;
- S9E+N43R+N76D+A194P+V205I+Q206L+Y209W+ S216V+N261M+L262E;
- S9E+N43R+I72A+N76D+A194P+Q206L+S259D+ L262E;
- S9E+N43R+N76D+A194P+V205I+Q206L+S259D+ L262E;
- S9E+N43R+N76D+H120V+Q182E+A194P+V205I+ Q206L+Y209W+S256D+S259D+N261W+L262E;
- S9E+N43R+N76D+A194P+V205I+Q206L+Y209W+ S259D+N261W+L262E;
- S9E+N43R+N76D+V205I+Q206L+Y209W+S259D+ N261W+L262E;
- S9E+N43R+N76D+Q182E+A194P+V205I+Q206L+ Y209W+S256D+S259D+N261W+L262E;
- S9E+N43R+N76D+H120V+Q182E+A194P+V205I+ Q206L+Y209W+S256D+N261W+L262E+*275aH+ *275bH;

S3V+N76D+H120V+Q182E+N185E+S188E+V205I+
Q206L+Y209W+S216V+S256D+N261W+L262E;
S9E+N43R+N76D+A158E+A194P+N204D+V205I+
Q206L+Y209W+S212G+S216V+L262E;
S9E+N43R+N76D+A158E+G160P+V205I+Q206L+
Y209W+S259D+N261W+L262E;
S9E+N43R+N76D+A158E+G160P+A194P+N204D+
V205I+Q206L+Y209W+S212G+S216V+L262E;
S9E+N43R+N76D+A158E+G160P+S161E+A194P+
N204D+V205I+Q206L+Y209W+S216V+L262E+
*275aH+*275bH;
S9E+N43R+N76D+A158E+G160P+S161E+A194P+
N204D+V205I+Q206L+Y209W+L262E;
S9E+N43R+N76D+A158E+G160P+S161E+A194P+
N204D+V205I+Q206L+Y209W+S212G+S216V+
L262E+*275aH+*275bH;
S9E+N43R+N76D+A158E+G160P+S161E+A194P+
N204D+V205I+Q206L+Y209W+S212G+L262E;
S9E+N43R+N76D+A158E+A194P+V205I+Q206L+
Y209W+S259D+N261W+L262E;
S9E+N43R+N76D+A158E+G160P+S161E+A194P+
N204D+V205I+Q206L+Y209W+S212G+L262E+
*275aH+*275bH;
S9E+N43R+N76D+A158E+G160P+S161E+A194P+
N204D+V205I+Q206L+Y209W+S216V+L262E;
S9E+N43R+N76D+A158E+G160P+S161E+A194P+
Q206L+Y209W+S259D+L262E+*275aH+*275bH;
S9E+N43R+N76D+A158E+G160P+S161E+A194P+
V205I+Q206L+Y209W+S212G+S216V+L262E;
S9E+N43R+N76D+A158E+S161E+V205I+Q206L+
Y209W+S259D+N261W+L262E;
S9E+N43R+N76D+A158E+G160P+S161E+V205I+
Q206L+Y209W+S259D+N261W+L262E;
S9E+N43R+N76D+A158E+S161E+A194P+N204D+
V205I+Q206L+Y209W+S212G+S216V+L262E;
S9E+N43R+N76D+G160P+V205I+Q206L+Y209W+
S259D+N261W+L262E;
S9E+N43R+N76D+A194P+N204D+V205I+Q206L+
Y209W+S212G+S216V+S259D+N261W+L262E;
S9E+N43R+N76D+A194P+Q206L+Y209W+L262E;
S9E+N43R+N76D+A194P+Q206L+Y209W+S256D+
S259D+N261W+L262E;
S9E+N43R+N76D+A194P+Q206L+Y209W+T255E+
S256D+S259D+T260E+N261W+L262E;
S9E+N43R+N76D+V205I+Q206L+Y209W+S259D+
N261W+L262E;
S9E+N43R+N76D+G115W+H120V+A194P+Q206L+
Y209W+S259D+L262E;
S9E+N43R+N76D+G115W+H120V+P129D+A194P+
Q206L+Y209W+S259D+L262E;
S9E+N43R+N76D+G160P+A194P+N204D+V205I+
Q206L+Y209W+S212G+S216V+L262E;
S9E+N43R+N76D+G160P+S161E+A194P+N204D+
V205I+Q206L+Y209W+S212G+S216V+L262E;
S9E+N43R+N76D+G160P+S161E+A194P+N204D+
V205I+Q206L+Y209W+S212G+S216V+L262E+
*275aH+*275bH;
S9E+N43R+N76D+N204D+V205I+Q206L+Y209W+
S259D+N261W+L262E;
S9E+N43R+N76D+G160P+S161E+V205I+Q206L+
Y209W+S259D+N261W+L262E;
S9E+N43R+N76D+H120V+Q182E+A194P+V205I+
Q206L+Y209W+S256D+N261W+L262E+*275aH+
*275bH;
S9E+N43R+N76D+V205I+Q206L+Y209W+S216V+
S259D+N261W+L262E;
S9E+N43R+N76D+S161E+V205I+Q206L+Y209W+
S259D+N261W+L262E;
S9E+N43R+N76D+P131*+A194P+Q206L+Y209W+
S259D+L262E;
S9E+N43R+N76D+H120V+Q182E+A194P+V205I+
Q206L+Y209W+S256D+N261W+L262E+*275aH+
*275bH;
S9E+N43R+N76D+S161E+A194P+N204D+V205I+
Q206L+Y209W+S212G+S216V+L262E+*275aH+
*275bH;
S9E+N43R+N76D+V205I+Q206L+Y209W+S212G+
S259D+N261W+L262E;
S9E+N43R+N76D+N204D+V205I+Q206L+Y209W+
S212G+S216V+S259D+N261W+L262E.

The protease variants of the present invention have improved stability in liquid cleaning composition at pH 10 and above when compared to the parent protease such as a protease with SEQ ID NO: 2. This makes these variants suitable for use in high pH liquid detergents for e.g. laundry or dish wash.

In one embodiment, the protease variant has improved stability, in particular improved storage stability in a high pH liquid cleaning composition, compared to the parent protease. In a preferred embodiment, the protease variant has improved stability, in particular improved storage stability, and on par or improved wash performance compared to the parent protease.

In an embodiment, the protease variant has improved storage stability in a high pH liquid detergent, and on par or improved wash performance compared to the parent protease wherein storage stability may be measured using an 'accelerated storage stability assay' and wash performance may be measured using the Automatic Mechanical Stress Assay (AMSA).

In an embodiment, the protease variant has at least 60% but less than 100% sequence identity to the parent protease. In an embodiment, the protease variant has at least 70% but less than 100% sequence identity to the parent protease. In an embodiment, the protease variant has at least 75% but less than 100% sequence identity to the parent protease. In an embodiment, the protease variant has at least 80% but less than 100% sequence identity to the parent protease. In an embodiment, the protease variant has at least 85% but less than 100% sequence identity to the parent protease. In an embodiment, the protease variant has at least 90% but less than 100% sequence identity to the parent protease. In an embodiment, the protease variant has at least 93% but less than 100% sequence identity to the parent protease. In an embodiment, the protease variant has at least 95% but less than 100% sequence identity to the parent protease. In an embodiment, the protease variant has at least 96% but less than 100% sequence identity to the parent protease. In an embodiment, the protease variant has at least 97% but less than 100% sequence identity to the parent protease. In an embodiment, the protease variant has at least 98% but less than 100% sequence identity to the parent protease.

In an embodiment, the variant has an amino acid sequence which is at least 60% identical to SEQ ID NO: 1, e.g., at least 60%, such as at least 70%, such as at least 80%, such as at least 90%, such as at least 95% sequence identity to the amino acid sequence of SEQ ID NO: 1.

In another embodiment, the variant has an amino acid sequence which is at least 60% identical to SEQ ID NO: 2, e.g., at least 60%, such as at least 70%, such as at least 80%, such as at least 90%, such as at least 95% sequence identity to the amino acid sequence of SEQ ID NO: 2.

In one aspect, the total number of alterations in the parent protease is between 3 and 30, preferably between 3 and 20, more preferably between 3 and 15, even more preferably between 3 and 10, most preferably between 3 and 8 alterations. In another aspect, total number of alterations in the parent protease is 3, 4, 5, 6, 7, 8, 9, 10, 11, 12, 13, 14, 15, 16, 17, 18, 19, 20, 21, 22, 23, 24, 25, 26, 27, 28, 29 or 30 alterations.

The parent or the precursor protease may be any protease or even more preferred any subtilase as defined below. The parent protease is preferably a protease having at least 60% identity to SEQ ID NO: 2 but the parent may be any serine protease. A serine protease is an enzyme which catalyzes the hydrolysis of peptide bonds, and in which there is an essential serine residue at the active site (White, Handler and Smith, 1973 "Principles of Biochemistry," Fifth Edition, McGraw-Hill Book Company, NY, pp. 271-272). The bacterial serine proteases have molecular weights in the 20,000 to 45,000 Dalton range. They are inhibited by diisopropylfluorophosphate. They hydrolyze simple terminal esters and are similar in activity to eukaryotic chymotrypsin, also a serine protease. Even more preferred parent is an alkaline protease, covering a sub-group, reflects the high pH optimum of some of the serine proteases, from pH 9.0 to 11.0 (for review, see Priest, 1977, *Bacteriological Rev.* 41: 711-753).

The parent protease may be a subtilase which is a subgroup of the serine proteases that has been proposed by Siezen et al., 1991, *Protein Eng.* 4:719-737 and Siezen et al., 1997, *Protein Science* 6:501-523. They are defined by homology analysis of more than 170 amino acid sequences of serine proteases previously referred to as subtilisin-like proteases. A subtilisin was previously often defined as a serine protease produced by Gram-positive bacteria or fungi, and according to Siezen et al. now is a subgroup of subtilases. A wide variety of subtilases have been identified, and the amino acid sequence of a number of subtilases has been determined. For a more detailed description of such subtilases and their amino acid sequences reference is made to Siezen et al. (1997). The subtilisin is as mentioned a subgroup of subtilases which are serine proteases from the family S8, in particular from the subfamily S8A, as defined by the MEROPS database (merops.sanger.ac.uk/cgi-bin/famsum?family=S8). Examples of subtilisins are Subtilisin BPN' (SEQ ID NO: 1) and subtilisin 309 (SEQ ID NO: 2) which have the MEROPS numbers S08.034 and S08.003, respectively. A parent protease may also be a subtilase isolated from a natural source, wherein subsequent modifications (such as replacement(s) of the amino acid side chain(s), substitution(s), deletion(s) and/or insertion(s)) have been made while retaining the characteristic of a subtilase. Furthermore, a parent protease may be a subtilase which has been prepared by the DNA shuffling technique, such as described by Ness et al., 1999, *Nature Biotechnology,* 17: 893-896.

Alternatively, the term "parent protease" may be termed "precursor protease" and is used to describe the starting protease into which mutations are made to obtain the variant of the invention. The parent protease is preferably of the subtilisin subgroups.

One subgroup of the subtilases, I-S1 or "true" subtilisins, include the "classical" subtilisins, such as subtilisin 168 (BSS168), subtilisin BPN', subtilisin Carlsberg (ALCAL-ASE®, Novozymes A/S), and subtilisin DY (BSSDY). BPN' is subtilisin BPN' from *B. amyloliquefaciens,* Subtilisin BPN' has the amino acid sequence of SEQ ID NO: 1. A further subgroup of the subtilases, I-S2 or high alkaline subtilisins, is recognized by Siezen et al. (supra). Sub-group I-S2 proteases are described as highly alkaline subtilisins and include enzymes such as subtilisin PB92 (BAALKP) (MAXACAL®, Genencor International Inc.), subtilisin 147 (BLS147) (ESPERASE®, Novozymes A/S), alkaline elastase YaB (BSEYAB) and subtilisin 309 (SAVINASE®, Novozymes A/S) having the amino acid sequence SEQ ID NO: 2.

The homology between two amino acid sequences is in this context described by the parameter "identity" for purposes of the present invention, the degree of identity between two amino acid sequences is determined using the Needleman-Wunsch algorithm as described above. The output from the routine is besides the amino acid alignment the calculation of the "Percent Identity" between the two sequences.

Based on this description it is routine for a person skilled in the art to identify suitable homologous subtilases, which can be modified according to the invention.

The parent protease may be a polypeptide having at least 60% sequence identity to the polypeptide of SEQ ID NO: 1, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 1. In another aspect, the parent comprises or consists of the amino acid sequence of SEQ ID NO: 1.

The parent protease may be a polypeptide having at least 60% sequence identity to the polypeptide of SEQ ID NO: 2, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have protease activity. In one aspect, the amino acid sequence of the parent differs by up to 10 amino acids, e.g., 1, 2, 3, 4, 5, 6, 7, 8, 9, or 10, from the polypeptide of SEQ ID NO: 2. In another aspect, the parent comprises or consists of the amino acid sequence of SEQ ID NO: 2.

The parent protease may be a hybrid polypeptide in which a region of one polypeptide is fused at the N-terminus or the C-terminus of a region of another polypeptide.

The parent protease may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial protease. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus,* or *Streptomyces* protease, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* protease.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* protease Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes.

Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

A high pH stable protease variant according to the invention may be prepared by a method, comprising the steps of:
(a) introducing into a parent protease the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D, wherein the positions corresponds to the positions of SEQ ID NO: 1, and
(b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., US 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7:127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The liquid cleaning compositions according the invention comprise in addition to the proteases according to the invention additional components such as the non-limiting components set forth below. The choice of components may include, for fabric care, the consideration of the type of fabric to be cleaned, the type and/or degree of soiling, the temperature at which cleaning is to take place, and the formulation of the detergent product.

In a particular embodiment, the high pH liquid cleaning composition comprises a protease variant of the invention and one or more detergent components, such as surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers.

The protease variants of the cleaning composition of the invention may be stabilized using conventional stabilizing agents and protease inhibitors, e.g., a polyol such as propylene glycol or glycerol, a sugar or sugar alcohol, different salts such as NaCl; KCl; lactic acid, formic acid, boric acid, or a boric acid derivative, e.g., an aromatic borate ester, or a phenyl boronic acid derivative such as 4-formylphenyl boronic acid (e.g. as in WO96/41859), or a peptide aldehyde such as di-, tri- or tetrapeptide aldehydes or aldehyde analogues (either of the form B1-B0-R wherein, R is H, CH3, CX3, CHX2, or CH2X (X=halogen), B0 is a single amino acid residue (preferably with an optionally substituted aliphatic or aromatic side chain); and 1 consists of one or more amino acid residues (preferably one, two or three), optionally comprising an N-terminal protection group (e.g. as in WO2009/118375, WO2013/004635), or as described in WO2005/105826, WO 2009/118375, WO 98/13459 or a protease inhibitor of the protein type such as RASI, BASI, WASI (bifunctional alpha-amylase/subtilisin inhibitors of rice, barley and wheat) (e.g. as in WO2009/095425) or C12 or SSI.

Furthermore, the use of peptide aldehydes for stabilizing certain proteases in liquid detergents has been disclosed in PCT publications WO94/04651 and WO98/13460. More specifically, WO94/04651 discloses the use of the peptide aldehydes Phe-Gly-Ala-PheH and Phe-Gly-Ala-LeuH for stabilizing subtilisin-type proteases. For stabilizing chymotrypsin-type proteases, WO94/04651 discloses Leu-Leu-TyrH as a suitable peptide aldehyde. Furthermore, WO94/04651 proposes methyl carbamate or methyl urea as an N-terminal protecting group of the peptide aldehydes. WO98/13460 discloses the use of peptide protease inhibitors, either peptide aldehydes or trifluromethyl ketones, where the peptide chain contains 2-5 amino acids and the aldehyde/trifluromethyl ketone is derived from the amino acids alanine, valine, isoleucine, leucine, phenylglycine, phenylalanine or homophenylalanine and where the N-terminal protection group is preferably a sulphonamide or amidophoshate. As an example CH3SO2Phe-Gly-Ala-LeuH can be used.

In another embodiment, a compound of the general formula I:

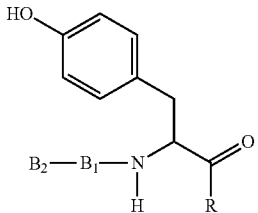

where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine; can be used for stabilizing and/or inhibiting a protease variant of the present invention.

In another embodiment, a protease inhibitor is a peptide compound of the formula B2-B1-B0-R wherein:
R is hydrogen, CH3, CX3, CHX2, or CH2X, wherein X is a halogen atom;
B0 is a phenylalanine residue with an OH substituent at the p-position and/or at the m-position;
B1 is a single amino acid residue; and
B2 consists of one or more amino acid residues, optionally comprising an N-terminal protection group.

Said protease inhibitor of the formula B2-B1-B0-R as described above can be used as an optional protease inhibitor in the sense of the present invention (e.g. in combination with or as part of any embodiment of the present invention as disclosed herein)

Thus, in another embodiment the invention relates to a liquid cleaning composition having pH 10 or above, comprising:
(a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10;
(b) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
(a) from 20% to 95% wt, preferably from 40% to 95% wt, further preferably from about 70% to about 90% wt water;
(b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10;
(c) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant; and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;
(d) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In said embodiment, (c1) and (c2) can be used as alternatives or in combination with each other.

Thus, in another embodiment the invention relates to a liquid cleaning composition having pH 10 or above, comprising:
- (a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO 1);
- (b) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
- (a) from 20% to 95% wt, preferably from 40% to 95% wt, further preferably from about 70% to about 90% wt water;
- (b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO 1);
- (c) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
- (a) from 0% to 20% wt, preferably 0.1% to 2.5% wt of a detergent surfactant;
- (b) from 0.001% to 10% wt, preferably 0.1% to 5% wt of a protease variant, preferably said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO 1); and
- (c1) from 20% to 95% wt, preferably from 40% to 95% wt, further preferably from about 70% to about 90% wt water; and/or
- (c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;
- (d) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In said embodiment, (c1) and (c2) can be used as alternatives or in combination with each other.

Thus, in another embodiment the invention relates to a liquid cleaning composition having pH 10 or above, comprising:
- (a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises substitutions at positions corresponding to the positions 205 and 209 of BPN' (SEQ ID NO: 1), further preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1);
- (b) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment the invention relates to a liquid cleaning composition comprising:
- (a) from 20% to 95% wt, preferably from 40% to 95% wt, further preferably from about 70% to about 90% wt water;
- (b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises substitutions at positions corresponding to the positions 205 and 209 of BPN' (SEQ ID NO: 1), further preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO 1);

(c) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment the invention relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant, preferably said variant comprises substitutions at positions corresponding to the positions 205 and 209 of BPN' (SEQ ID NO: 1), further preferably said variant comprises substitutions at positions corresponding to the positions 205 and 209 of BPN' (SEQ ID NO: 1) and a substitution at one or more positions selected from the positions corresponding to the positions 3, 9, 18, 43, 49, 61, 76, 115, 120, 182, 185, 188, 194, 206, 216, 217, 218, 222, 255, 256, 259, 260, 261 and 262 of BPN' (SEQ ID NO: 1); and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;
(d) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In said embodiment, (c1) and (c2) can be used as alternatives or in combination with each other.

Thus, in another embodiment the invention relates to a liquid cleaning composition having pH 10 or above, comprising:
(a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO 1);
(b) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
(d) from 20% to 95% wt, preferably from 40% to 95% wt, further preferably from about 70% to about 90% wt water;
(e) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO 1);
(f) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:
(a) from 0% to 20% wt, preferably 0.1% to 2.5% wt of a detergent surfactant;
(b) from 0.001% to 10% wt, preferably 0.1% to 5% wt of a protease variant, preferably said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO 1); and
(c1) from 20% to 95% wt, preferably from 40% to 95% wt, further preferably from about 70% to about 90% wt water; and/or
(c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;

(d) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In said embodiment, (c1) and (c2) can be used as alternatives or in combination with each other.

Thus, in another embodiment the invention relates to a liquid cleaning composition having pH 10 or above, comprising:

(a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises substitutions corresponding to the substitutions X205I and X209W of BPN' (SEQ ID NO 1), further preferably said variant comprises substitutions corresponding to the substitutions X205I and X209W of BPN' (SEQ ID NO 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO 1);

(b) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:

(a) from 20% to 95% wt, preferably from 40% to 95% wt, further preferably from about 70% to about 90% wt water;

(b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10, preferably said variant comprises substitutions corresponding to the substitutions X205I and X209W of BPN' (SEQ ID NO 1), further preferably said variant comprises substitutions corresponding to the substitutions X205I and X209W of BPN' (SEQ ID NO 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO 1);

(c) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In another embodiment, the invention relates to a liquid cleaning composition comprising:

(a) from 0% to 20% wt, preferably 0.1% to 2.5% wt of a detergent surfactant;

(b) from 0.001% to 10% wt, preferably 0.1% to 5% wt of a protease variant, preferably said variant comprises substitutions corresponding to the substitutions X205I and X209W of BPN' (SEQ ID NO: 1), further preferably said variant comprises substitutions corresponding to the substitutions X205I and X209W of BPN' (SEQ ID NO 1) and one or more substitutions corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X206L, X216V, X217M, X218T, X222S, X255E, X255D, X256D, X256E, X259D, X259E, X260A, X260E, X260D, X261M, X261W, X262E and X262D of BPN' (SEQ ID NO 1); and (c1) from 20% to 95% wt, preferably from 40% to 95% wt, further preferably from about 70% to about 90% wt water; and/or (c2) from 1% to 30% wt of an alkaline buffer system comprising an alkali metal silicate or an alkali metal hydroxide or a mixture thereof, to provide a pH of from about 11 to 13.5, preferably the pH is from about 12 to 13.5;

(d) optionally, a protease inhibitor, preferably said protease inhibitor is a peptide aldehyde protease inhibitor, further preferably said protease inhibitor is a compound of the general formula I, where R is selected from the group consisting of hydrogen, CH3, CX3, CHX2, CH2X, where X is a halogen atom, 1 is a single amino acid residue and B2 is one or more amino acid residues, B2 optionally comprising an N-terminal protection group, with the proviso that if 1 is leucine then B2 cannot be leucine.

In said embodiment, (c1) and (c2) can be used as alternatives or in combination with each other.

In some preferred embodiments, the protease variant is selected from the group consisting of:
S9E+N43R+G61E+N76D+G115W+H120V+A194P+ Q206L+S259D+L262E;
S9E+N43R+N76D+A194P+V205I+Q206L+Y209W+ S259D+N261W+L262E;
S9E+N43R+N76D+Q182E+A194P+V205I+Q206L+ Y209W+S259D+N261W+L262E;
S9E+N43R+N76D+A194P+V205I+Q206L+Y209W+ S216V+M222S+L262E;

S9E+N43R+N76D+A194P+V205I+Q206L+S256D+
S259D+N261W+L262E;
S9E+N18S+N43R+N76D+G115W+H120V+A194P+
V205I+Q206L+S259D+L262E;
S9E+N43R+N76D+G115W+H120V+A194P+V205I+
Q206L+S259D+L262E;
S9E+N43R+N76D+A194P+V205I+Q206L+Y209W+
S259D+N261W+L262E;
S9E+N43R+N76D+A194P+V205I+Q206L+S256D+
S259D+N261W+L262E;
S9E+N43R+N76D+Q182E+A194P+V205I+Q206L+
Y209W+S256D+S259D+N261W+L262E;
S9E+N43R+N76D+S188E+A194P+V205I+Q206L+
Y209W+S216V+L262E;
S9E+N76D+G115W+G160P+Q182E+V205I+Q206L+
Y209W+S256D+T260E+N261W+L262E;
S9E+N43R+N76D+H120T+A194P+Q206L+S256D+
S259D+N261W+L262E;
S9E+N43R+N76D+H120T+A194P+V205I+Q206L+
Y209W+S216V+L262E;
S9E+N76D+G160P+Q182E+V205I+Q206L+Y209W+
S256D+N261W+L262E;
S9E+N43R+N76D+Q182E+A194P+V205I+Q206L+
S259D+N261W+L262E;
S9E+N76D+Q182E+V205I+Q206L+Y209W+S256D+
N261W+L262E;
S9E+N43R+N76D+Q182E+A194P+V205I+Q206L+
S259D+N261W+L262E+*275aH;
S9E+N43R+N76D+Q182E+N185E+S188E+A194P+
Q206L+Y209W+S259D+L262E;
S9E+N43R+N76D+N185E+A194P+V205I+Q206L+
Y209W+S216V+L262E;
S9E+N43R+N76D+A194P+V205I+Q206L+Y209W+
S216V+N261M+L262E;
S9E+N43R+I72A+N76D+A194P+Q206L+S259D+
L262E;
S9E+N43R+N76D+A194P+V205I+Q206L+S259D+
L262E;
S9E+N43R+N76D+H120V+Q182E+A194P+V205I+
Q206L+Y209W+S256D+S259D+N261W+L262E;
S9E+N43R+N76D+A194P+V205I+Q206L+Y209W+
S259D+N261W+L262E;
S9E+N43R+N76D+V205I+Q206L+Y209W+S259D+
N261W+L262E;
S9E+N43R+N76D+Q182E+A194P+V205I+Q206L+
Y209W+S256D+S259D+N261W+L262E;
S9E+N43R+N76D+H120V+Q182E+A194P+V205I+
Q206L+Y209W+S256D+N261W+L262E+*275aH+
*275bH;
S3V+N76D+H120V+Q182E+N185E+S188E+V205I+
Q206L+Y209W+S216V+S256D+N261W+L262E;
S9E+N43R+N76D+A158E+A194P+N204D+V205I+
Q206L+Y209W+S212G+S216V+L262E;
S9E+N43R+N76D+A158E+G160P+V205I+Q206L+
Y209W+S259D+N261W+L262E;
S9E+N43R+N76D+A158E+G160P+A194P+N204D+
V205I+Q206L+Y209W+S212G+S216V+L262E;
S9E+N43R+N76D+A158E+G160P+S161E+A194P+
N204D+V205I+Q206L+Y209W+S216V+L262E+
*275aH+*275bH;
S9E+N43R+N76D+A158E+G160P+S161E+A194P+
N204D+V205I+Q206L+Y209W+L262E;
S9E+N43R+N76D+A158E+G160P+S161E+A194P+
N204D+V205I+Q206L+Y209W+S212G+S216V+L262E+
*275aH+*275bH;
S9E+N43R+N76D+A158E+G160P+S161E+A194P+
N204D+V205I+Q206L+Y209W+S212G+L262E;
S9E+N43R+N76D+A158E+A194P+V205I+Q206L+
Y209W+S259D+N261W+L262E;
S9E+N43R+N76D+A158E+G160P+S161E+A194P+
N204D+V205I+Q206L+Y209W+S212G+L262E+
*275aH+*275bH;
S9E+N43R+N76D+A158E+G160P+S161E+A194P+
N204D+V205I+Q206L+Y209W+S216V+L262E;
S9E+N43R+N76D+A158E+G160P+S161E+A194P+
Q206L+Y209W+S259D+L262E+*275aH+*275bH;
S9E+N43R+N76D+A158E+G160P+S161E+A194P+
V205I+Q206L+Y209W+S212G+S216V+L262E;
S9E+N43R+N76D+A158E+S161E+V205I+Q206L+
Y209W+S259D+N261W+L262E;
S9E+N43R+N76D+A158E+G160P+S161E+V205I+
Q206L+Y209W+S259D+N261W+L262E;
S9E+N43R+N76D+A158E+S161E+A194P+N204D+
V205I+Q206L+Y209W+S212G+S216V+L262E;
S9E+N43R+N76D+G160P+V205I+Q206L+Y209W+
S259D+N261W+L262E;
S9E+N43R+N76D+A194P+N204D+V205I+Q206L+
Y209W+S212G+S216V+S259D+N261W+L262E;
S9E+N43R+N76D+A194P+Q206L+Y209W+L262E;
S9E+N43R+N76D+A194P+Q206L+Y209W+S256D+
S259D+N261W+L262E;
S9E+N43R+N76D+A194P+Q206L+Y209W+T255E+
S256D+S259D+T260E+N261W+L262E;
S9E+N43R+N76D+V205I+Q206L+Y209W+S259D+
N261W+L262E;
S9E+N43R+N76D+G115W+H120V+A194P+Q206L+
Y209W+S259D+L262E;
S9E+N43R+N76D+G115W+H120V+P129D+A194P+
Q206L+Y209W+S259D+L262E;
S9E+N43R+N76D+G160P+A194P+N204D+V205I+
Q206L+Y209W+S212G+S216V+L262E;
S9E+N43R+N76D+G160P+S161E+A194P+N204D+
V205I+Q206L+Y209W+S212G+S216V+L262E;
S9E+N43R+N76D+G160P+S161E+A194P+N204D+
V205I+Q206L+Y209W+S212G+S216V+L262E+*275aH+
*275bH;
S9E+N43R+N76D+N204D+V205I+Q206L+Y209W+
S259D+N261W+L262E;
S9E+N43R+N76D+G160P+S161E+V205I+Q206L+
Y209W+S259D+N261W+L262E;
S9E+N43R+N76D+H120V+Q182E+A194P+V205I+
Q206L+Y209W+S256D+N261W+L262E+*275aH+
*275bH;
S9E+N43R+N76D+V205I+Q206L+Y209W+S216V+
S259D+N261W+L262E;
S9E+N43R+N76D+S161E+V205I+Q206L+Y209W+
S259D+N261W+L262E;
S9E+N43R+N76D+P131*+A194P+Q206L+Y209W+
S259D+L262E;
S9E+N43R+N76D+H120V+Q182E+A194P+V205I+
Q206L+Y209W+S256D+N261W+L262E+*275aH+
*275bH;
S9E+N43R+N76D+S161E+A194P+N204D+V205I+
Q206L+Y209W+S212G+S216V+L262E+*275aH+
*275bH;
S9E+N43R+N76D+V205I+Q206L+Y209W+S212G+
S259D+N261W+L262E;
S9E+N43R+N76D+N204D+V205I+Q206L+Y209W+
S212G+S216V+S259D+N261W+L262E.

The composition may be formulated as described in, e.g., WO 92/19709, WO 92/19708 and U.S. Pat. No. 6,472,364. In some embodiments, the enzymes employed herein are stabilized by the presence of water-soluble sources of zinc (II), calcium (II) and/or magnesium (II) ions in the finished compositions that provide such ions to the enzymes, as well as other metal ions (e.g., barium (II), scandium (II), iron (II), manganese (II), aluminum (Ill), Tin (II), cobalt (II), copper (II), Nickel (II), and oxovanadium (IV).

A protease variant of the present invention may also be incorporated in the detergent formulations disclosed in WO 97/07202, which is hereby incorporated by reference.

A liquid cleaning composition of the invention is characterised by having high pH (at or above pH 10). The liquid high pH cleaning composition may further comprise high amount of water. In one preferred aspect of the invention, the liquid cleaning composition comprises:

(a) from 0% to 20% wt, preferably 0.1% to 2.5% wt of a detergent surfactant;
(b) from 40% to 95% wt, preferably from about 70% to about 90% wt water;
(c) from 1% to 30% wt of an alkaline buffer system comprising an alkali metal silicate or an alkali metal hydroxide or a mixture thereof, to provide a pH of from about 11 to 13.5; and
(d) from 0.001% to 10% wt, preferably 0.1% to 5% wt of a protease variant.

The surfactants may be anionic and/or cationic and/or non-ionic and/or semi-polar and/or zwitterionic, or a mixture thereof. In a particular embodiment, the cleaning composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. When included in a cleaning composition according to the invention the surfactants will usually contain from about 1% to about 40% by weight, such as from about 1% to about 20%, preferably from about 0% to about 5% by weight. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diyl-bis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included the cleaning composition according to the invention it will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

Non-limiting examples of zwitterionic surfactants include betaine, alkyldimethylbetaine, sulfobetaine, and combinations thereof.

Particularly preferred surfactants include LAS, MES, alcohol ether sulfate, ethoxylated lauryl alcohol or sodium dodecylbenzenesulfonate.

A liquid high pH cleaning composition according to the invention, typically contain at least 20% by weight and up to 95% by weight water, such as up to about 70% wt water, up to about 65% wt water, up to about 55% wt water, up to about 45% wt water, up to about 35% wt water. Other types of liquids, including without limitation, alkanols, amines, diols, ethers and polyols may be included in the liquid cleaning composition. The cleaning composition may contain from 0-30% organic solvent.

The cleaning composition may also contain a hydrotrope which is a compound that solubilizes hydrophobic compounds in aqueous solutions (or oppositely, polar substances in a non-polar environment). Typically, hydrotropes have both hydrophilic and hydrophobic characters (so-called amphiphilic properties as known from surfactants); however the molecular structure of hydrotropes generally do not favor spontaneous self-aggregation, see, e.g., review by Hodgdon and Kaler, 2007, *Current Opinion in Colloid & Interface Science* 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behavior, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in cleaning compositions allows for example more concentrated formulations of surfactants (as in the process of compacting liquid detergents by removing water) without inducing undesired phenomena such as phase separation or high viscosity. The cleaning composition according to the invention may contain 0-5% by weight, such as about 0.5 to about 5%, or about 3% to about 5% wt, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof. The cleaning composition according to the invention may contain about 0-65% by weight, such as about 5% to about 45% of a detergent builder or co-builder, or a mixture thereof. In a dish wash detergent, the level of builder is typically 40-65%, particularly 50-65%. Builders and chelators soften, e.g., the wash water by removing the metal ions from the liquid. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2''-nitrilotriethanol), and carboxymethyl inulin (CMI), and combinations thereof.

The cleaning composition according to the invention may also contain 0-20% by weight, such as about 5% to about 10% wt, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly (acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis (methylenephosphonic acid) (DTPMPA or DTMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N', N'-triacetate (HEDTA), diethanolglycine (DEG), diethylenetriamine penta (methylenephosphonic acid) (DTPMP), aminotris (methylenephosphonic acid) (ATMP), and combinations and salts thereof. Further exemplary builders and/or co-builders are described in, e.g., WO 2009/102854 and U.S. Pat. No. 5,977,053.

The cleaning composition according to the invention may contain 0-50% by weight, such as about 0.1% to about 25%, of a bleaching system. Bleach systems remove discolor often by oxidation, and many bleaches also have strong bactericidal properties, and are used for disinfecting and sterilizing. Any bleaching system known in the art for use in laundry detergents may be utilized. Suitable bleaching system components include bleaching catalysts, hypochlorite, photobleaches, bleach activators, sources of hydrogen peroxide such as sodium percarbonate and sodium perborates, preformed peracids and mixtures thereof.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn (O)3Mn(Me3-TACN)](PF6)2, and [2,2',2''-nitrilotris(ethane-1,2-diylazanylylidene-κN-methanylylidene)triphenolato-κ3O]manganese(III). The bleach catalysts may also be other metal compounds, such as iron or cobalt complexes.

Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetraacetylethylene diamine (TAED), sodium 4-[(3,5,5-trimethylhexanoyl)oxy] benzene sulfonate (ISONOBS), diperoxy dodecanoic acid, 4-(dodecanoyloxy)benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO 98/17767. A particular family of bleach activators was disclosed in EP 624154 and particulary acetyl triethyl citrate (ATC). ATC or a short chain triglyceride like triacetin has the advantage that it is environmental friendly as it eventually degrades into citric acid and alcohol. Furthermore, acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido) peroxyhexanoic acid (PAP). The bleaching system may also include a bleach catalyst.

In some embodiments, the bleach component may be an organic catalyst selected from the group consisting of organic catalysts having the following formula:

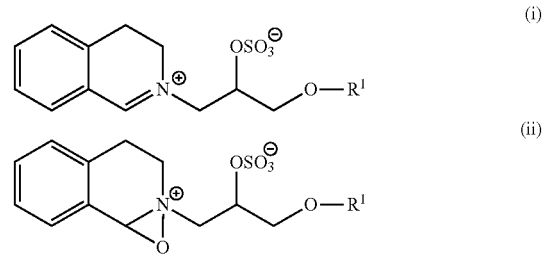

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO 2007/087258, WO 2007/087244, WO 2007/087259 and WO 2007/087242. Suitable photobleaches may for example be sulfonated zinc phthalocyanine.

One particular bleaching agent is hypochlorite such as sodium hypochlorite (NaClO). Hypochlorite is stabilized by high pH and in addition hypochlorite is antibacterial. In general, a cleaning composition according to the invention contains 3-8% sodium hypochlorite and 0.01-0.05% sodium hydroxide; the sodium hydroxide is used to slow the decomposition of sodium hypochlorite into sodium chloride and sodium chlorate. The hypochlorite may not be part of a detergent formula but a separate product added during the wash process.

In one aspect of the invention, a high pH cleaning composition of the invention does not comprise any bleach agents i.e. the cleaning composition may be bleach free.

The cleaning composition according to the invention may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. The cleaning compositions of the present invention may also include fabric hueing agents such as dyes or pigments, which when formulated in detergent compositions can deposit onto a fabric when the fabric is contacted with a wash liquor comprising the detergent compositions and thus altering the tint of the fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/003274, WO 2005/003275, WO 2005/003276 and EP 1876226 (hereby incorporated by reference). The detergent composition preferably comprises from about 0.00003 wt. % to about 0.2 wt. %, from about 0.00008 wt. % to about 0.05 wt. %, or even from about 0.0001 wt. % to about 0.04 wt. % fabric hueing agent. The composition may comprise from 0.0001 wt % to 0.2 wt. % fabric hueing agent, this may be especially preferred when the composition is in the form of a unit dose pouch. Suitable hueing agents are also disclosed in, e.g., WO 2007/087257 and WO 2007/087243.

The cleaning composition according to the invention may comprise one or more (additional) enzymes such as an amylase, perhydrolase, arabinase, carbohydrase, cellulase (e.g., endoglucanase), cutinase, galactanase, haloperoxygenase, lipase, mannanase, oxidase, e.g., laccase and/or peroxidase, pectinase, pectin lyases, protease, DNases, xylanase, xanthanase, and xyloglucanase.

In general, the properties of the selected enzyme(s) should be compatible with detergent (i.e., pH-optimum, compatibility with other enzymatic and non-enzymatic ingredients, etc.), and the enzyme(s) should be present in effective amounts.

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Commercially available cellulases include Celluzyme™, and Carezyme™ (Novozymes A/S), Clazinase™, and Puradax HA™ (Genencor International Inc.), and KAC-500(B)™ (Kao Corporation).

The composition may comprise one or more additional proteases including those of bacterial, fungal, plant, viral or animal origin, e.g., vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from, e.g., family M4 or other metalloprotease such as those from M5, M7 or M8 families.

Examples of metalloproteases are the neutral metalloprotease as described in WO 2007/044993 (Genencor Int.) such as those derived from *Bacillus amyloliquefaciens*.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® (Novozymes A/S), those sold under the tradename Maxatase®, Maxacal®, Maxapem®, Purafect®, Purafect Prime®, Purafect MA®, Purafect Ox®, Purafect OxP®, Puramax®, Properase®, FN2®, FN3®, FN4®, Excellase®, Eraser®, Opticlean® and Optimase® (Danisco/DuPont), Axapem™ (Gist-Brocades N.V.), BLAP (sequence shown in FIG. 29 of U.S. Pat. No. 5,352,604) and variants hereof (Henkel AG) and KAP (*Bacillus alkalophilus* subtilisin) from Kao.

Suitable lipases and cutinases include those of bacterial or fungal origin. Chemically modified or protein engineered mutant enzymes are included. Examples include lipase from *Thermomyces*, e.g., from *T. lanuginosus* (previously named *Humicola lanuginosa*) as described in EP 258068 and EP 305216, cutinase from *Humicola*, e.g., *H. insolens* (WO 96/13580), lipase from strains of *Pseudomonas* (some of these now renamed to *Burkholderia*), e.g., *P. alcaligenes* or *P. pseudoalcaligenes* (EP 218272), *P. cepacia* (EP 331376), *P.* sp. strain SD705 (WO 95/06720 & WO 96/27002), *P. wisconsinensis* (WO 96/12012), GDSL-type *Streptomyces* lipases (WO 2010/065455), cutinase from *Magnaporthe grisea* (WO 2010/107560), cutinase from *Pseudomonas mendocina* (U.S. Pat. No. 5,389,536), lipase from *Thermobifida fusca* (WO 2011/084412), *Geobacillus stearothermophilus* lipase (WO 2011/084417), lipase from *Bacillus subtilis* (WO 2011/084599), and lipase from *Streptomyces griseus* (WO 2011/150157) and *S. pristinaespiralis* (WO 2012/137147). Preferred commercial lipase products include Lipolase™ Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g., acyltransferases with homology to *Candida antarctica* lipase A (WO 2010/111143), acyltransferase from *Mycobacterium smegmatis* (WO 2005/056782), perhydrolases from the CE 7 family (WO 2009/067279), and variants of the *M. smegmatis* perhydrolase in particular the S54V variant used in the commercial product Gentle Power Bleach from Huntsman Textile Effects Pte Ltd (WO 2010/100028).

Suitable amylases may be an alpha-amylase or a glucoamylase and may be of bacterial or fungal origin. Chemically modified or protein engineered mutants are included. Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in the cleaning composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Any detergent components known in the art for use in laundry cleaning compositions may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

The cleaning compositions of the present invention can also contain dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

The cleaning compositions of the present invention will preferably also contain additional components that may tint articles being cleaned, such as fluorescent whitening agent or optical brighteners. Where present the brightener is preferably at a level of about 0.01% to about 05%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt. % to upper levels of 0.5 or even 0.75 wt. %.

The cleaning compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 03/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

The cleaning compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

The cleaning composition of the invention may be formulated into pouches which can be configured as single or multicompartments. It can be of any form, shape and material which is suitable for hold the composition, e.g., without allowing the release of the composition from the pouch prior to water contact. The pouch is made from water soluble film which encloses an inner volume. The inner volume can be divided into compartments of the pouch. Preferred films are polymeric materials preferably polymers which are formed into a film or sheet. Preferred polymers, copolymers or derivates thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. of Gary, Indiana, US) plus plasticisers like glycerol, ethylene glycerol, Propylene glycol, sorbitol and mixtures thereof. The pouches can comprise a solid laundry detergent composition or part components and/or a liquid cleaning composition or part components separated by the water soluble film. The compartment for liquid components can be different in composition than compartments containing solids. See, e.g., US 2009/0011970.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

The present invention is also directed to methods for using the cleaning compositions according to the invention in laundering of textile and fabrics, such as house hold laundry washing and industrial laundry washing. Such methods includes methods for using the compositions according to the invention or compositions thereof in cleaning hard surfaces such as floors, tables, walls, roofs etc. as well as surfaces of hard objects such as cars (car wash) and dishes (dish wash).

The protease variants of the present invention may be added to and thus become a component of the high pH cleaning composition according to the invention. Thus one aspect of the invention relates to the use of a protease variant in a high pH cleaning process such as laundering and/or hard surface cleaning at pH at or above pH 10.

A cleaning composition of the present invention may be formulated, for example, as a hand or machine laundry detergent composition including a laundry additive composition suitable for pre-treatment of stained fabrics and a rinse added fabric softener composition, or be formulated as a detergent composition for use in general household hard surface cleaning operations, or be formulated for hand or machine dishwashing operations.

The cleaning process or the textile care process may for example be a laundry process, a dishwashing process or cleaning of hard surfaces such as bathroom tiles, floors, table tops, drains, sinks and washbasins. Laundry processes can for example be household laundering, but it may also be industrial laundering. Furthermore, the invention relates to a process for laundering of fabrics and/or garments where the process comprises treating fabrics with a washing solution containing a high pH cleaning composition according to the invention, and at least one protease variant of the invention. The cleaning process or a textile care process can for example be carried out in a machine washing process, in a manual washing process or in a pre-spotter process. The washing solution can for example be an aqueous washing solution containing a cleaning composition.

The invention further concerns the use of cleaning compositions of the invention in a proteinaceous stain removing processes. The proteinaceous stains may be stains such as food stains, e.g., baby food, sebum, cocoa, egg, blood, milk, ink, grass, or a combination hereof.

A preferred embodiment concerns a method of cleaning, the method comprising the steps of: contacting an object with a high pH cleaning composition comprising a protease variant of the invention under conditions suitable for cleaning the object. In a preferred embodiment the cleaning composition is used in a laundry or a dish wash process.

Still another embodiment relates to a method for removing stains from fabric or dishware which comprises contacting the fabric or dishware with a high pH cleaning composition comprising a protease of the invention under conditions suitable for cleaning the object.

Also contemplated are compositions and methods of treating fabrics (e.g., to desize a textile) using the cleaning composition of the invention. The high pH cleaning composition can be used in any fabric-treating method which is well known in the art (see, e.g., U.S. Pat. No. 6,077,316). For example, in one aspect, the feel and appearance of a fabric is improved by a method comprising contacting the fabric with a protease in a solution. In one aspect, the fabric is treated with the solution under pressure.

The high pH cleaning composition of the present invention is suited for use in liquid laundry and liquid hard surface applications, including dish wash and car wash. Accordingly, the present invention includes a method for laundering a fabric or washing a hard surface. The method comprises the steps of contacting the fabric/dishware to be cleaned with a solution comprising the high pH cleaning composition according to the invention. The fabric may comprise any fabric capable of being laundered in normal consumer use conditions. The hard surface may comprise any dishware such as crockery, cutlery, ceramics, plastics such as melamine, metals, china, glass, acrylics or other hard surfaces such as cars, floors etc. The solution preferably has a pH from about 9 to about 13.5. The compositions may be employed at concentrations from about 100 ppm, preferably 500 ppm to about 15,000 ppm in solution. The water temperatures typically range from about 5° C. to about 95° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In some preferred embodiments, the high pH cleaning compositions provided herein are typically formulated such that, during use in aqueous cleaning operations, the wash water has a pH of from about 9 to about 13.5, or in alternative embodiments, or from about 10 to about 13.5 even from about 11 to about 13.5. In some preferred embodiments the liquid laundry products are formulated to have a pH from about 12 to about 13.5. Techniques for controlling pH at recommended usage levels include the use of buffers, acids, alkalis, etc., and are well known to those skilled in the art. In the context of the present invention alkalis are used to adjust pH to about 9 to 13.5 preferably about 10 to 13.5.

The Invention is Further Summarized in the Below Paragraphs:

1. A liquid cleaning composition having pH 10 or above, comprising:
   (a) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 10
   (b) optionally, a protease inhibitor, preferably said protease inhibitor is a peptide aldehyde protease inhibitor.
2. A liquid cleaning composition comprising:
   (a) from 20% to 95% wt, preferably from 40% to 95% wt, further preferably from about 70% to about 90% wt water;
   (b) at least 0.01 wt % protease, wherein the protease is a variant of a parent protease and wherein the protease variant has an amino acid sequence which has at least 60% sequence identity to the amino acid sequence of SEQ ID NO: 2 and wherein said protease variant is characterized by having at least 10% higher residual activity than the parent protease when measured after 4 hours at 40° C. in liquid detergent with pH 7.5 or above, preferably 10;
   (c) optionally, a protease inhibitor, preferably said protease inhibitor is a peptide aldehyde protease inhibitor.
3. The liquid cleaning composition of paragraph 1, wherein said pH is from about 12 to 13.5.
4. The liquid cleaning composition of any of paragraphs 1-3, wherein the protease is a variant of a protease having at least 60% identity with the amino acid sequence of SEQ ID NO: 2 wherein said variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1).
5. The liquid cleaning composition of any of paragraphs 1-4, wherein the protease is a variant of a protease having at least 60% identity with the amino acid sequence of SEQ ID NO: 2 wherein said variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1).
6. The liquid cleaning composition of any of paragraphs 1-5, wherein the variant comprises one more substitution corresponding to the substitutions X209W, X262E, X76D, X194P, X204D, X206L.
7. The liquid cleaning composition according to any of the preceding paragraphs, wherein the variant has an amino acid sequence which is at least 60% identical to SEQ ID NO: 2, e.g., at least 60%, such as at least 70%, such as at least 80%, such as at least 90%, such as at least 95% sequence identity to the amino acid sequence of SEQ ID NO: 2.
8. The liquid cleaning composition according to any of the preceding paragraphs, wherein said protease variant has storage stability at 40° C. greater than at least one stabilized protease variant selected from the group consisting of:
S9E+N43R+N76D+G115W+H120V+A194P+Q206L+S259D+L262E;
S9E+N43R+N76D+A194P+V205I+Q206L+S259D+N261W+L262E;
S9E+N43R+N76D+Q182E+A194P+V205I+Q206L+S259D+N261W+L262E;
S9E+N43R+N76D+A194P+V205I+Q206L+Y209W+S216V+L262E;
S9E+N43R+N76D+A194P+Q206L+S256D+S259D+N261W+L262E;
S9E+N18S+N43R+N76D+G115W+H120V+A194P+Q206L+S259D+L262E;
S9E+N43R+N76D+G115W+H120V+A194P+Q206L+S259D+L262E;
S9E+N43R+N76D+A194P+Q206L+Y209W+S259D+N261W+L262ES9E+N43R+N76D+A194P+V205I+Q206L+S259D+N261W+L262E;
S9E+N43R+N76D+Q182E+A194P+V205I+Q206L+Y209W+S259D+N261W+L262E;
S9E+N43R+N76D+A194P+V205I+Q206L+Y209W+S216V+L262E;
S9E+N76D+G115W+G160P+Q182E+V205I+Q206L+Y209W+S256D+N261W+L262E;

S9E+N43R+N76D+A194P+Q206L+S256D+S259D+ N261W+L262E;
S9E+N43R+N76D+A194P+V205I+Q206L+Y209W+ S216V+L262E;
S9E+N76D+Q182E+V205I+Q206L+Y209W+S256D+ N261W+L262E;
S9E+N43R+N76D+A194P+V205I+Q206L+S259D+ N261W+L262E;
S9E+N76D+V205I+Q206L+Y209W+S256D+N261W+ L262E;
S9E+N43R+N76D+A194P+V205I+Q206L+S259D+ N261W+L262E+*275aH;
S9E+N43R+N76D+N185E+S188E+A194P+Q206L+ Y209W+S259D+L262E;
S9E+N43R+N76D+A194P+V205I+Q206L+Y209W+ S216V+L262E;
S9E+N43R+N76D+A194P+V205I+Q206L+Y209W+ S216V+L262E;
S9E+N43R+I72A+N76D+A194P+Q206L+L262E;
S9E+N43R+N76D+A194P+V205I+Q206L+L262E.

9. The liquid cleaning composition according to any of the preceding paragraphs, wherein said protease variant is selected from the group consisting of:
S9E+N43R+G61E+N76D+G115W+H120V+A194P+ Q206L+S259D+L262E;
S9E+N43R+N76D+A194P+V205I+Q206L+Y209W+ S259D+N261W+L262E;
S9E+N43R+N76D+Q182E+A194P+V205I+Q206L+ Y209W+S259D+N261W+L262E;
S9E+N43R+N76D+A194P+V205I+Q206L+Y209W+ S216V+M222S+L262E;
S9E+N43R+N76D+A194P+V205I+Q206L+S256D+ S259D+N261W+L262E;
S9E+N18S+N43R+N76D+G115W+H120V+A194P+ V205I+Q206L+S259D+L262E;
S9E+N43R+N76D+G115W+H120V+A194P+V205I+ Q206L+S259D+L262E;
S9E+N43R+N76D+A194P+V205I+Q206L+Y209W+ S259D+N261W+L262E;
S9E+N43R+N76D+A194P+V205I+Q206L+S256D+ S259D+N261W+L262E;
S9E+N43R+N76D+Q182E+A194P+V205I+Q206L+ Y209W+S256D+S259D+N261W+L262E;
S9E+N43R+N76D+S188E+A194P+V205I+Q206L+ Y209W+S216V+L262E;
S9E+N76D+G115W+G160P+Q182E+V205I+Q206L+ Y209W+S256D+T260E+N261W+L262E;
S9E+N43R+N76D+H120T+A194P+Q206L+S256D+ S259D+N261W+L262E;
S9E+N43R+N76D+H120T+A194P+V205I+Q206L+ Y209W+S216V+L262E;
S9E+N76D+G160P+Q182E+V205I+Q206L+Y209W+ S256D+N261W+L262E;
S9E+N43R+N76D+Q182E+A194P+V205I+Q206L+ S259D+N261W+L262E;
S9E+N76D+Q182E+V205I+Q206L+Y209W+S256D+ N261W+L262E;
S9E+N43R+N76D+Q182E+A194P+V205I+Q206L+ S259D+N261W+L262E+*275aH;
S9E+N43R+N76D+Q182E+N185E+S188E+A194P+ Q206L+Y209W+S259D+L262E;
S9E+N43R+N76D+N185E+A194P+V205I+Q206L+ Y209W+S216V+L262E;
S9E+N43R+N76D+A194P+V205I+Q206L+Y209W+ S216V+N261M+L262E;
S9E+N43R+I72A+N76D+A194P+Q206L+S259D+ L262E;
S9E+N43R+N76D+A194P+V205I+Q206L+S259D+ L262E;
S9E+N43R+N76D+H120V+Q182E+A194P+V205I+ Q206L+Y209W+S256D+S259D+N261W+L262E;
S9E+N43R+N76D+A194P+V205I+Q206L+Y209W+ S259D+N261W+L262E;
S9E+N43R+N76D+V205I+Q206L+Y209W+S259D+ N261W+L262E;
S9E+N43R+N76D+Q182E+A194P+V205I+Q206L+ Y209W+S256D+S259D+N261W+L262E;
S9E+N43R+N76D+H120V+Q182E+A194P+V205I+ Q206L+Y209W+S256D+N261W+L262E+*275aH+ *275bH;
S3V+N76D+H120V+Q182E+N185E+S188E+V205I+ Q206L+Y209W+S216V+S256D+N261W+L262E;
S9E+N43R+N76D+A158E+A194P+N204D+V205I+ Q206L+Y209W+S212G+S216V+L262E;
S9E+N43R+N76D+A158E+G160P+V205I+Q206L+ Y209W+S259D+N261W+L262E;
S9E+N43R+N76D+A158E+G160P+A194P+N204D+ V205I+Q206L+Y209W+S212G+S216V+L262E;
S9E+N43R+N76D+A158E+G160P+S161E+A194P+ N204D+V205I+Q206L+Y209W+S216V+L262E+ *275aH+*275bH;
S9E+N43R+N76D+A158E+G160P+S161E+A194P+ N204D+V205I+Q206L+Y209W+L262E;
S9E+N43R+N76D+A158E+G160P+S161E+A194P+ N204D+V205I+Q206L+Y209W+S212G+S216V+ L262E+*275aH+*275bH;
S9E+N43R+N76D+A158E+G160P+S161E+A194P+ N204D+V205I+Q206L+Y209W+S212G+L262E;
S9E+N43R+N76D+A158E+A194P+V205I+Q206L+ Y209W+S259D+N261W+L262E;
S9E+N43R+N76D+A158E+G160P+S161E+A194P+ N204D+V205I+Q206L+Y209W+S212G+L262E+ *275aH+*275bH;
S9E+N43R+N76D+A158E+G160P+S161E+A194P+ N204D+V205I+Q206L+Y209W+S216V+L262E;
S9E+N43R+N76D+A158E+G160P+S161E+A194P+ Q206L+Y209W+S259D+L262E+*275aH+*275bH;
S9E+N43R+N76D+A158E+G160P+S161E+A194P+ V205I+Q206L+Y209W+S212G+S216V+L262E;
S9E+N43R+N76D+A158E+S161E+V205I+Q206L+ Y209W+S259D+N261W+L262E;
S9E+N43R+N76D+A158E+G160P+S161E+V205I+ Q206L+Y209W+S259D+N261W+L262E;
S9E+N43R+N76D+A158E+S161E+A194P+N204D+ V205I+Q206L+Y209W+S212G+S216V+L262E;
S9E+N43R+N76D+G160P+V205I+Q206L+Y209W+ S259D+N261W+L262E;
S9E+N43R+N76D+A194P+N204D+V205I+Q206L+ Y209W+S212G+S216V+S259D+N261W+L262E;
S9E+N43R+N76D+A194P+Q206L+Y209W+L262E;
S9E+N43R+N76D+A194P+Q206L+Y209W+S256D+ S259D+N261W+L262E;
S9E+N43R+N76D+A194P+Q206L+Y209W+T255E+ S256D+S259D+T260E+N261W+L262E;
S9E+N43R+N76D+V205I+Q206L+Y209W+S259D+ N261W+L262E;
S9E+N43R+N76D+G115W+H120V+A194P+Q206L+ Y209W+S259D+L262E;
S9E+N43R+N76D+G115W+H120V+P129D+A194P+ Q206L+Y209W+S259D+L262E;
S9E+N43R+N76D+G160P+A194P+N204D+V205I+ Q206L+Y209W+S212G+S216V+L262E;
S9E+N43R+N76D+G160P+S161E+A194P+N204D+ V205I+Q206L+Y209W+S212G+S216V+L262E;

S9E+N43R+N76D+G160P+S161E+A194P+N204D+
V205I+Q206L+Y209W+S212G+S216V+L262E+*275aH+
*275bH;
S9E+N43R+N76D+N204D+V205I+Q206L+Y209W+
S259D+N261W+L262E;
S9E+N43R+N76D+G160P+S161E+V205I+Q206L+
Y209W+S259D+N261W+L262E;
S9E+N43R+N76D+H120V+Q182E+A194P+V205I+
Q206L+Y209W+S256D+N261W+L262E+*275aH+
*275bH;
S9E+N43R+N76D+V205I+Q206L+Y209W+S216V+
S259D+N261W+L262E;
S9E+N43R+N76D+S161E+V205I+Q206L+Y209W+
S259D+N261W+L262E;
S9E+N43R+N76D+P131*+A194P+Q206L+Y209W+
S259D+L262E;
S9E+N43R+N76D+H120V+Q182E+A194P+V205I+
Q206L+Y209W+S256D+N261W+L262E+*275aH+
*275bH;
S9E+N43R+N76D+S161E+A194P+N204D+V205I+
Q206L+Y209W+S212G+S216V+L262E+*275aH+
*275bH;
S9E+N43R+N76D+V205I+Q206L+Y209W+S212G+
S259D+N261W+L262E;
S9E+N43R+N76D+N204D+V205I+Q206L+Y209W+
S212G+S216V+S259D+N261W+L262E.

10. A liquid cleaning composition comprising:
   (a) from 0% to 20% wt, preferably 0.1% to 2.5% wt of a detergent surfactant;
   (b) from 0.001% to 10% wt, preferably 0.1% to 5% wt of a protease variant; and
   (c1) from 20% to 95% wt, preferably from 40% to 95% wt, further preferably from about 70% to about 90% wt water; and/or
   (c2) from 1% to 30% wt of an alkaline buffer system comprising an alkali metal silicate or an alkali metal hydroxide or a mixture thereof, to provide a pH of from about 7.5 to 13.5, preferably the pH is from about 12 to 13.5;
   (d) optionally, a protease inhibitor, preferably said protease inhibitor is a peptide aldehyde protease inhibitor.

11. The liquid cleaning composition of paragraph 10, wherein the protease variant comprises a substitution at one or more positions selected from the positions corresponding to the positions 3, 9, 18, 43, 49, 61, 76, 115, 120, 182, 185, 188, 194, 205, 206, 209, 216, 217, 218, 222, 255, 256, 259, 260, 261 and 262 of BPN' (SEQ ID NO: 1).

12. The liquid cleaning composition according to paragraph 11, wherein the protease variant comprises one more substitution corresponding to the substitutions X3V, X9D, X9E, X18S, X43R, X43K, X49T, X61D, X76D, X115W, X120T, X120V, X120D, X182D, X182E, X185E, X185D, X188E, X188D, X194P, X205I, X206L, X209W, X216V, X217M, X218T, X222S, X255E, X255D, X256D, X256E, X259D, X259E, X260A, X260E, X260D, X261M, X261W, X262E and X262D of BPN' (SEQ ID NO: 1).

13. The liquid cleaning composition according to any of paragraphs 10 to 12, wherein the protease variant has at least 60%, e.g., at least 65%, at least 70%, at least 75%, at least 80%, at least 85%, at least 90%, at least 95%, at least 96%, at least 97%, at least 98% but less than 100% sequence identity to the polypeptide of SEQ ID NO: 2.

14. The liquid cleaning composition according to any of paragraphs 10-13, wherein said protease variant is selected from the group consisting of:
S9E+N43R+G61E+N76D+G115W+H120V+A194P+
Q206L+S259D+L262E;
S9E+N43R+N76D+A194P+V205I+Q206L+Y209W+
S259D+N261W+L262E;
S9E+N43R+N76D+Q182E+A194P+V205I+Q206L+
Y209W+S259D+N261W+L262E;
S9E+N43R+N76D+A194P+V205I+Q206L+Y209W+
S216V+M222S+L262E;
S9E+N43R+N76D+A194P+V205I+Q206L+S256D+
S259D+N261W+L262E;
S9E+N18S+N43R+N76D+G115W+H120V+A194P+
V205I+Q206L+S259D+L262E;
S9E+N43R+N76D+G115W+H120V+A194P+V205I+
Q206L+S259D+L262E;
S9E+N43R+N76D+A194P+V205I+Q206L+Y209W+
S259D+N261W+L262E;
S9E+N43R+N76D+A194P+V205I+Q206L+S256D+
S259D+N261W+L262E;
S9E+N43R+N76D+Q182E+A194P+V205I+Q206L+
Y209W+S256D+S259D+N261W+L262E;
S9E+N43R+N76D+S188E+A194P+V205I+Q206L+
Y209W+S216V+L262E;
S9E+N76D+G115W+G160P+Q182E+V205I+Q206L+
Y209W+S256D+T260E+N261W+L262E;
S9E+N43R+N76D+H120T+A194P+Q206L+S256D+
S259D+N261W+L262E;
S9E+N43R+N76D+H120T+A194P+V205I+Q206L+
Y209W+S216V+L262E;
S9E+N76D+G160P+Q182E+V205I+Q206L+Y209W+
S256D+N261W+L262E;
S9E+N43R+N76D+Q182E+A194P+V205I+Q206L+
S259D+N261W+L262E;
S9E+N76D+Q182E+V205I+Q206L+Y209W+S256D+
N261W+L262E;
S9E+N43R+N76D+Q182E+A194P+V205I+Q206L+
S259D+N261W+L262E+*275aH;
S9E+N43R+N76D+Q182E+N185E+S188E+A194P+
Q206L+Y209W+S259D+L262E;
S9E+N43R+N76D+N185E+A194P+V205I+Q206L+
Y209W+S216V+L262E;
S9E+N43R+N76D+A194P+V205I+Q206L+Y209W+
S216V+N261M+L262E;
S9E+N43R+I72A+N76D+A194P+Q206L+S259D+
L262E;
S9E+N43R+N76D+A194P+V205I+Q206L+S259D+
L262E;
S9E+N43R+N76D+H120V+Q182E+A194P+V205I+
Q206L+Y209W+S256D+S259D+N261W+L262E;
S9E+N43R+N76D+A194P+V205I+Q206L+Y209W+
S259D+N261W+L262E;
S9E+N43R+N76D+V205I+Q206L+Y209W+S259D+
N261W+L262E;
S9E+N43R+N76D+Q182E+A194P+V205I+Q206L+
Y209W+S256D+S259D+N261W+L262E;
S9E+N43R+N76D+H120V+Q182E+A194P+V205I+
Q206L+Y209W+S256D+N261W+L262E+*275aH+
*275bH;
S3V+N76D+H120V+Q182E+N185E+S188E+V205I+
Q206L+Y209W+S216V+S256D+N261W+L262E;
S9E+N43R+N76D+A158E+A194P+N204D+V205I+
Q206L+Y209W+S212G+S216V+L262E;
S9E+N43R+N76D+A158E+G160P+V205I+Q206L+
Y209W+S259D+N261W+L262E;

S9E+N43R+N76D+A158E+G160P+A194P+N204D+
V205I+Q206L+Y209W+S212G+S216V+L262E;
S9E+N43R+N76D+A158E+G160P+S161E+A194P+
N204D+V205I+Q206L+Y209W+S216V+L262E+
*275aH+*275bH;
S9E+N43R+N76D+A158E+G160P+S161E+A194P+
N204D+V205I+Q206L+Y209W+L262E;
S9E+N43R+N76D+A158E+G160P+S161E+A194P+
N204D+V205I+Q206L+Y209W+S212G+S216V+L262E+
*275aH+*275bH;
S9E+N43R+N76D+A158E+G160P+S161E+A194P+
N204D+V205I+Q206L+Y209W+S212G+L262E;
S9E+N43R+N76D+A158E+A194P+V205I+Q206L+
Y209W+S259D+N261W+L262E;
S9E+N43R+N76D+A158E+G160P+S161E+A194P+
N204D+V205I+Q206L+Y209W+S212G+L262E+
*275aH+*275bH;
S9E+N43R+N76D+A158E+G160P+S161E+A194P+
N204D+V205I+Q206L+Y209W+S216V+L262E;
S9E+N43R+N76D+A158E+G160P+S161E+A194P+
Q206L+Y209W+S259D+L262E+*275aH+*275bH;
S9E+N43R+N76D+A158E+G160P+S161E+A194P+
V205I+Q206L+Y209W+S212G+S216V+L262E;
S9E+N43R+N76D+A158E+S161E+V205I+Q206L+
Y209W+S259D+N261W+L262E;
S9E+N43R+N76D+A158E+G160P+S161E+V205I+
Q206L+Y209W+S259D+N261W+L262E;
S9E+N43R+N76D+A158E+S161E+A194P+N204D+
V205I+Q206L+Y209W+S212G+S216V+L262E;
S9E+N43R+N76D+G160P+V205I+Q206L+Y209W+
S259D+N261W+L262E;
S9E+N43R+N76D+A194P+N204D+V205I+Q206L+
Y209W+S212G+S216V+S259D+N261W+L262E;
S9E+N43R+N76D+A194P+Q206L+Y209W+L262E;
S9E+N43R+N76D+A194P+Q206L+Y209W+S256D+
S259D+N261W+L262E;
S9E+N43R+N76D+A194P+Q206L+Y209W+T255E+
S256D+S259D+T260E+N261W+L262E;
S9E+N43R+N76D+V205I+Q206L+Y209W+S259D+
N261W+L262E;
S9E+N43R+N76D+G115W+H120V+A194P+Q206L+
Y209W+S259D+L262E;
S9E+N43R+N76D+G115W+H120V+P129D+A194P+
Q206L+Y209W+S259D+L262E;
S9E+N43R+N76D+G160P+A194P+N204D+V205I+
Q206L+Y209W+S212G+S216V+L262E;
S9E+N43R+N76D+G160P+S161E+A194P+N204D+
V205I+Q206L+Y209W+S212G+S216V+L262E;
S9E+N43R+N76D+G160P+S161E+A194P+N204D+
V205I+Q206L+Y209W+S212G+S216V+L262E+*275aH+
*275bH;
S9E+N43R+N76D+N204D+V205I+Q206L+Y209W+
S259D+N261W+L262E;
S9E+N43R+N76D+G160P+S161E+V205I+Q206L+
Y209W+S259D+N261W+L262E;
S9E+N43R+N76D+H120V+Q182E+A194P+V205I+
Q206L+Y209W+S256D+N261W+L262E+*275aH+
*275bH;
S9E+N43R+N76D+V205I+Q206L+Y209W+S216V+
S259D+N261W+L262E;
S9E+N43R+N76D+S161E+V205I+Q206L+Y209W+
S259D+N261W+L262E;
S9E+N43R+N76D+P131*+A194P+Q206L+Y209W+
S259D+L262E;
S9E+N43R+N76D+H120V+Q182E+A194P+V205I+
Q206L+Y209W+S256D+N261W+L262E+*275aH+
*275bH;
S9E+N43R+N76D+S161E+A194P+N204D+V205I+
Q206L+Y209W+S212G+S216V+L262E+*275aH+
*275bH;
S9E+N43R+N76D+V205I+Q206L+Y209W+S212G+
S259D+N261W+L262E;
S9E+N43R+N76D+N204D+V205I+Q206L+Y209W+
S212G+S216V+S259D+N261W+L262E.

15. The cleaning composition according to any of the preceding paragraphs, which comprises one or more additional enzymes selected from the group comprising of amylases, catalases, cellulases (e.g., endoglucanases), cutinases, haloperoxygenases, lipases, mannanases, pectinases, pectin lyases, peroxidases, proteases, xanthanases, and xyloglucanases, or any mixture thereof.

16. Use of the liquid cleaning composition of any of the preceding paragraphs in a cleaning process such as laundry or hard surface cleaning including dish wash and industrial cleaning.

17. The use of paragraph 16, wherein the laundry process is selected from a group consisting of: a residential laundry process, an industrial laundry process and an institutional laundry process.

The present invention is further described by the following examples that should not be construed as limiting the scope of the invention.

EXAMPLES

Materials and Methods
Suc-AAPF-pNA Activity Assay

Proteolytic activity can be determined by a method employing Suc-AAPF-PNA as the substrate. Suc-AAPF-PNA is an abbreviation for N-Succinyl-Alanine-Alanine-Proline-Phenylalanine-p-Nitroanilide, and is a blocked peptide which can be cleaved by endo-proteases. Following cleavage a free PNA molecule is liberated which has a yellow color and thus can be measured by visible spectrophotometry at wavelength 405 nm. The Suc-AAPF-PNA substrate is manufactured by Bachem (cat. no. L1400, dissolved in DMSO).

The protease sample to be analyzed is diluted in residual activity buffer (100 mM Tris pH 8.6). The assay is performed by transferring 3 0 µl of diluted enzyme samples to 96 well microtiter plate and adding 70 µl substrate working solution (0.72 mg/ml in 100 mM Tris pH8.6). The solution was mixed at room temperature and absorption is measured every 20 seconds over 5 minutes at OD 405 nm.

The slope (absorbance per minute) of the time dependent absorption-curve is directly proportional to the activity of the protease in question under the given set of conditions. The protease sample is diluted to a level where the slope was linear.

Example 1: Preparation and Expression of Protease Variants

The following summarizes the mutation and introduction of an expression cassette into Bacillus subtilis. All DNA manipulations were done by PCR (e.g., Sambrook et al.; Molecular Cloning; Cold Spring Harbor Laboratory Press).

Recombinant B. subtilis constructs encoding protease variants were used to inoculate shakeflasks containing a rich media (e.g., 100 g/L sucrose (Danisco cat.no. 109-0429), 40 g/L crust soy (soy bean flour), 10 g/L $Na_2HPO_4.12H_2O$ (Merck cat.no. 6579), 0.1 ml/L replace-Dowfax63N10 (Dow). Cultivation typically takes 4 days at 30° C. shaking with 220 rpm.

Example 2: Purification of Protease Variants

The culture broth was centrifuged at 26000×g for 20 minutes and the supernatant was carefully decanted from the precipitate. The supernatant was filtered through a Nalgene 0.2 µm filtration unit in order to remove the rest of the *Bacillus* host cells. The pH in the 0.2 µm filtrate was adjusted to pH 8 with 3 M Tris base and the pH adjusted filtrate was applied to a MEP Hypercel column (Pall Corporation) equilibrated in 20 mM Tris/HCl, 1 mM CaCl$_2$, pH 8.0. After washing the column with the equilibration buffer, the column was step-eluted with 20 mM CH$_3$COOH/NaOH, 1 mM CaCl$_2$, pH 4.5. Fractions from the column were analyzed for protease activity using the Suc-AAPF-pNA assay at pH 9 and peak-fractions were pooled. The pH of the pool from the MEP Hypercel column was adjusted to pH 6 with 20% (v/v) CH$_3$COOH or 3 M Tris base and the pH adjusted pool was diluted with deionized water to the same conductivity as 20 mM MES/NaOH, 2 mM CaCl$_2$, pH 6.0. The diluted pool was applied to a SP-Sepharose® Fast Flow column (GE Healthcare) equilibrated in 20 mM MES/NaOH, 2 mM CaCl$_2$, pH 6.0. After washing the column with the equilibration buffer, the protease variant was eluted with a linear NaCl gradient (0 →0.5 M) in the same buffer over five column volumes. Fractions from the column were analyzed for protease activity using the Suc-AAPF-pNA assay at pH 9 and active fractions were analyzed by SDS-PAGE. Fractions, where only one band was observed on the Coomassie stained SDS-PAGE gel, were pooled as the purified preparation and was used for further experiments.

Example 3: Accelerated Storage Stability Assay

Storage stability of protease variants in liquid detergent was evaluated using an accelerated assay with incubation at elevated temperatures for up to 24 hours.

All purified protease samples were diluted to concentrations of 0.2 and 0.1 mg/ml based on absorbance at 280 nm and theoretical extinction coefficient using 0.01% Triton X-100. For each variant 2 wells with high protease concentration and 2 wells with low concentration were included. As reference Savinase (SEQ ID NO 2) or a stabilized protease variant was included on each microtiter plate. 30 µl protease sample was mixed with 270 µl detergent (Surf Sparkling Ocean, DC-2014-0009) in the well of a microtiter plate (Nunc U96 PP 0.5 ml) using a magnetic bar (on Zephyr pipetting station (Caliper LifeSciences) for 30 min). 20 µl of this mixture was then transferred to another microtiter plate (Nunc U96 PP 0.5 ml with added magnetic bars) and mixed with 150 µl 100 mM Tris pH 8.6 (at least 5 min on Zephyr). 30 µl of this dilution was transferred to a Nunc F 96-MTP, and after addition of 70 µl substrate solution initial activity of unstressed sample was determined by measuring absorbance at 405 nm every 20 sec for 5 min (on a SpectraMax Plus). After sealing, the detergent plate was incubated at 50° C. and pH 11 in an Eppendorf Thermomixer (no shaking). After 1, 3-4 and 23-24 hours incubation, 20 µl samples were withdrawn and residual activity of stressed sample was measured as with the initial, unstressed activity.

Decrease in activity during incubation with detergent was assumed to be exponential. Half lifes (T½) were found from linear regression of Log(Activity) versus incubation time. Savinase (SEQ ID NO 2) has a very short half life under the conditions of this experiment and therefore the effects of the mutations were measured relative to an already stabilized protease variant.

Accelerated Storage Stability at 40° C. of Variants T % IF: Half Life Improvement Effect of Single Mutations
Mutation G61E
S9E+N43R+N76D+G115W+H120V+A194P+Q206L+ S259D+L262E, T½: 0.9
S9E+N43R+G61E+N76D+G115W+H120V+A194P+ Q206L+S259D+L262E, T½: 4.8
Mutation Y209W
S9E+N43R+N76D+A194P+V205I+Q206L+S259D+ N261W+L262E, T½: 4.5
S9E+N43R+N76D+A194P+V205I+Q206L+Y209W+ S259D+N261W+L262E, T½: 13.0
S9E+N43R+N76D+Q182E+A194P+V205I+Q206L+ S259D+N261W+L262E, T½: 4.6
S9E+N43R+N76D+Q182E+A194P+V205I+Q206L+ Y209W+S259D+N261W+L262E, T½: 12.4
Mutation M222S
S9E+N43R+N76D+A194P+V205I+Q206L+Y209W+ S216V+L262E, T½: 12.0
S9E+N43R+N76D+A194P+V205I+Q206L+Y209W+ S216V+M222S+L262E, T½: 14.5
Mutation V205I
S9E+N43R+N76D+A194P+Q206L+T255E+S256D+ S259D+T260E+N261W+L262E, T½: 5.0
S9E+N43R+N76D+A194P+V205I+Q206L+T255E+ S256D+S259D+T260E+N261W+L262E, T½: 1.2
S9E+N43R+N76D+N117H+H120D+A194P+Q206L+ S259D+L262E, T½: 5.0
S9E+N43R+N76D+N117H+H120D+A194P+V205I+ Q206L+S259D+L262E, T½: 1.6
S9E+N43R+N76D+A194P+Q206L+S256D+S259D+ N261W+L262E, T½: 3.0
S9E+N43R+N76D+A194P+V205I+Q206L+S256D+ S259D+N261W+L262E, T½: 6.6
S9E+N18S+N43R+N76D+G115W+H120V+A194P+ Q206L+S259D+L262E, T½: 1.0
S9E+N18S+N43R+N76D+G115W+H120V+A194P+ V205I+Q206L+S259D+L262E, T½: 4.6
S9E+N43R+N76D+G115W+H120V+A194P+Q206L+ S259D+L262E, T½: 0.9
S9E+N43R+N76D+G115W+H120V+A194P+V205I+ Q206L+S259D+L262E, T½: 5.0
S9E+N43R+N76D+A194P+Q206L+Y209W+S259D+ N261W+L262E, T½: 9.9
S9E+N43R+N76D+A194P+V205I+Q206L+Y209W+ S259D+N261W+L262E, T½: 13.0
Mutation S256D
S9E+N43R+N76D+A194P+V205I+Q206L+S259D+ N261W+L262E, T½: 4.5
S9E+N43R+N76D+A194P+V205I+Q206L+S256D+ S259D+N261W+L262E, T½: 6.6
S9E+N43R+N76D+Q182E+A194P+V205I+Q206L+ Y209W+S259D+N261W+L262E, T½: 12.4
S9E+N43R+N76D+Q182E+A194P+V205I+Q206L+ Y209W+S256D+S259D+N261W+L262E, T½: 13.3
Mutation S188E
S9E+N43R+N76D+A194P+V205I+Q206L+Y209W+ S216V+L262E, T½: 12.0
S9E+N43R+N76D+S188E+A194P+V205I+Q206L+ Y209W+S216V+L262E, T½: 13.7
Mutation T260E
S9E+N76D+G115W+G160P+Q182E+V205I+Q206L+ Y209W+S256D+N261W+L262E, T½: 13.5

S9E+N76D+G115W+G160P+Q182E+V205I+Q206L+Y209W+S256D+T260E+N261W+L262E, T½: 15.1
Mutation H120T
S9E+N43R+N76D+A194P+Q206L+S256D+S259D+N261W+L262E, T½: 3.0
S9E+N43R+N76D+H120T+A194P+Q206L+S256D+S259D+N261W+L262E, T½: 5.4
S9E+N43R+N76D+A194P+V205I+Q206L+Y209W+S216V+L262E, T½: 12.0
S9E+N43R+N76D+H120T+A194P+V205I+Q206L+Y209W+S216V+L262E, T½: 12.2
Mutation G160P
S9E+N76D+Q182E+V205I+Q206L+Y209W+S256D+N261W+L262E, T½: 13.2
S9E+N76D+G160P+Q182E+V205I+Q206L+Y209W+S256D+N261W+L262E, T½: 14.3
Mutation Q182E
S9E+N43R+N76D+A194P+V205I+Q206L+S259D+N261W+L262E, T½: 4.5
S9E+N43R+N76D+Q182E+A194P+V205I+Q206L+S259D+N261W+L262E, T½: 4.6
S9E+N76D+V205I+Q206L+Y209W+S256D+N261W+L262E, T½: 12.3
S9E+N76D+Q182E+V205I+Q206L+Y209W+S256D+N261W+L262E, T½: 13.2
S9E+N43R+N76D+A194P+V205I+Q206L+S259D+N261W+L262E+*275aH, T½: 4.2
S9E+N43R+N76D+Q182E+A194P+V205I+Q206L+S259D+N261W+L262E+*275aH, T½: 4.6
S9E+N43R+N76D+N185E+S188E+A194P+Q206L+Y209W+S259D+L262E, T½: 11.5
S9E+N43R+N76D+Q182E+N185E+S188E+A194P+Q206L+Y209W+S259D+L262E, T½: 14.0
Mutation N185E
S9E+N43R+N76D+A194P+V205I+Q206L+Y209W+S216V+L262E, T½: 12.0
S9E+N43R+N76D+N185E+A194P+V205I+Q206L+Y209W+S216V+L262E, T½: 12.4
Mutation N261M
S9E+N43R+N76D+A194P+V205I+Q206L+Y209W+S216V+L262E, T½: 12.0
S9E+N43R+N76D+A194P+V205I+Q206L+Y209W+S216V+N261M+L262E, T½: 12.7
Mutation S259D
S9E+N43R+I72A+N76D+A194P+Q206L+L262E, T½: 6.0
S9E+N43R+I72A+N76D+A194P+Q206L+S259D+L262E, T½: 7.2
S9E+N43R+N76D+A194P+V205I+Q206L+L262E, T½: 6.0
S9E+N43R+N76D+A194P+V205I+Q206L+S259D+L262E, T½: 6.5

Example 4: Full Scale Wash Results for the Proteases of the Invention

The wash performance of the proteases of the invention was tested in full scale wash. The wash performance was tested on 22 different stains at a dosage response in laundry liquid detergent.

After washing and rinsing the swatches were spread out flat and allowed to air dry at room temperature overnight. All washes were evaluated the day after the wash. Light reflectance evaluations of the swatches were done using a Macbeth Color Eye 7000 reflectance spectrophotometer with very small aperture. The measurements were made without UV in the incident light and remission at 460 nm was extracted. Measurements were made on unwashed and washed swatches. The test swatch to be measured was placed on top of another swatch of same type and color.

Calculating the enzyme effect was done by taking the measurements from washed swatches with enzymes and subtract with the measurements from washed without enzyme for each stain, $\Delta \text{Rem}_{enzyme}$. Wash performance is expressed as a delta remission value ($\Delta \text{Rem}$).

The experiments were conducted with the detergent composition and swatches under the experimental conditions as specified in Table 21 below.

TABLE 21

| Experimental conditions for full scale wash laundry experiments | |
|---|---|
| Detergent dosage | Purex (Henkel) 45 g/wash |
| | Arm & Hammer (C&D) 45 g/wash |
| | Xtra (C&D) 45 g/wash |
| | Triple Clean (SUN) 45 g/wash |
| | ALL Free & Clear (SUN) 45 g/wash |
| Test solution volume | 63 L |
| pH | As is |
| Wash time | 12 min main wash, 2 rinses |
| Temperature | 30/15° C. |
| Water hardness | 6.7° dH |
| Protease concentration | 0.25, 0.5, 1 wt % |
| Swatches | |

Water hardness was adjusted to 6.7° dH by addition of CaCl2, MgCl2, and NaHCO$_3$(Ca2+:Mg2+:CO3−=3:1:6) to the test system.

TABLE 22

Delta remission value of detergent comprising proteases compared to detergent without protease at 15° C. in all Free & Clear (The enzymes tested were the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E):

| | Delta (vs blank) | | | | | | | | |
|---|---|---|---|---|---|---|---|---|---|
| Enzyme dose % | 0.25% | | | 0.50% | | | 1.00% | | |
| Enzymes | 1 | 2 | 3 | 1 | 2 | 3 | 1 | 2 | 3 |
| 108KC ACD sheep blood-dbl app | 0.3 | 0.9 | 0.5 | 1.3 | 0.3 | 1.3 | 1.1 | 1.6 | 0.8 |
| Blood, Hard set | 0.7 | 0.3 | 0.8 | 1.6 | 1.7 | 1.0 | 1.4 | 2.2 | 1.1 |
| Blood, Soft set (Cotton/Polyester) | −0.7 | 2.0 | −1.7 | −0.8 | −0.1 | 2.5 | 1.2 | −0.8 | 0.9 |
| CS-01 Aged blood | −0.9 | −0.1 | −0.2 | −1.0 | −0.1 | −0.6 | 0.6 | −0.3 | −0.3 |
| EMPA111 Blood | −0.3 | 0.3 | −0.5 | −0.4 | −0.6 | −0.3 | −0.3 | 0.4 | −0.2 |
| 062KC Rubbed in grass | 0.7 | 1.5 | 0.7 | 1.3 | 0.1 | 1.2 | 0.7 | 2.5 | 1.0 |
| 062PE Rubbed in grass | 1.2 | 0.4 | −0.2 | 2.0 | −0.5 | 0.2 | 0.7 | 1.5 | 0.7 |
| C-H039 Squeezed Grass | 0.5 | 0.9 | 0.9 | 0.8 | −0.2 | 0.5 | 0.6 | 1.3 | 0.4 |

TABLE 22-continued

Delta remission value of detergent comprising proteases compared to
detergent without protease at 15° C. in all Free & Clear (The enzymes tested were the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E):

| | Delta (vs blank) | | | | | | | | |
|---|---|---|---|---|---|---|---|---|---|
| Enzyme dose % | 0.25% | | | 0.50% | | | 1.00% | | |
| Enzymes | 1 | 2 | 3 | 1 | 2 | 3 | 1 | 2 | 3 |
| CS-08 Grass Extract | −0.2 | −0.2 | 0.1 | −0.1 | 0.1 | 0.0 | 0.1 | −0.4 | 0.3 |
| EMPA164 Grass | 0.6 | 0.5 | −0.2 | 0.8 | 0.7 | −0.2 | 0.9 | 0.4 | 0.6 |
| Grass, cotton | −0.1 | 0.6 | 0.0 | 0.3 | 0.0 | 0.7 | 0.7 | 1.4 | 0.9 |
| NZ Grass CN Grass | 0.9 | 0.6 | −0.6 | −0.3 | 1.1 | 0.9 | 1.0 | 0.8 | 1.3 |
| PCS-8 Grass Extract | 0.2 | 0.1 | −0.1 | −0.2 | −0.1 | 0.0 | 0.0 | 0.0 | 0.2 |
| C-05 BMI | 0.0 | 0.6 | −0.3 | 0.9 | 0.3 | 1.1 | 0.6 | 1.2 | 1.6 |
| EMPA 116 BMI © | 0.4 | −0.6 | 0.4 | 1.7 | 1.3 | 1.3 | 2.8 | 2.4 | 1.7 |
| EMPA 117 BMI (P/C) | 0.4 | 1.2 | −0.2 | 2.3 | 0.9 | 1.8 | 3.7 | 3.1 | 3.1 |
| 038KC Choc. Milk | 0.5 | 0.0 | 0.4 | 0.5 | −0.4 | 0.9 | 0.0 | 0.4 | 1.1 |
| PC-03 Choc. Milk/carbon black | 0.6 | 0.2 | 0.0 | 1.1 | 0.4 | 0.5 | 1.5 | 1.1 | 1.1 |
| 051KC Egg | 0.0 | −0.1 | 0.2 | −0.3 | 0.0 | 0.0 | 0.5 | 0.0 | 0.0 |
| W10N Whole Egg | 1.4 | 0.9 | 1.0 | 1.8 | 1.6 | 1.5 | 2.2 | 2.1 | 2.0 |
| French's brown gravy (contains wheat protein, beef extract) | 0.7 | 0.6 | 0.3 | 1.1 | 0.7 | 0.4 | 0.9 | 0.7 | 0.6 |
| KC-H172 Meat pate | 0.8 | 2.2 | 0.3 | 2.1 | 0.8 | 2.1 | 1.9 | 2.2 | 0.8 |

TABLE 23

Delta remission value of detergent comprising proteases compared to detergent without protease at 30° C.
in all Free & Clear (The enzymes tested in "Results (Enzymes-Blank)" below were the following:
1: S9E+N43R+N76D+V205I+Q206L+Y209W+S259D+N261W+L262E;
2: S9E+N43R+N76D+Q182E+A194P+V205I+Q206L+Y209W+S256D+S259D+N261W+ L262E;
3: S9E+N43R+N76D+H120V+Q182E+A194P+V205I+Q206L+Y209W+S256D+N261W+L262E+*275aH+*275bH;
4: S3V+N76D+H120V+Q182E+N185E+S188E+V205I+Q206L+Y209W+S216V+S256D+N261W+L262E):

All free and clear 30° C.

| | | Ref: Detergent blank | | | | | | | |
|---|---|---|---|---|---|---|---|---|---|
| | Results | 0.50% | | | | 1% | | | |
| | (Enzymes-Blank) | 1 | 2 | 3 | 4 | 1 | 2 | 3 | 4 |
| Blood | 108KC ACD sheep blood-dbl app | 3.3 | 2.8 | 2.5 | 2.2 | 4.5 | 4.0 | 4.0 | 3.2 |
| | Blood, Hard set | 1.9 | 1.1 | 1.4 | 0.9 | 3.3 | 1.8 | 2.4 | 1.4 |
| | Blood, Soft set (Cotton/Polyester) | 1.6 | 1.3 | 2.0 | 0.9 | 1.9 | 2.1 | 2.4 | 1.8 |
| | CS-01 Aged blood | 1.7 | 2.2 | 2.8 | 2.0 | 3.5 | 3.2 | 3.7 | 2.3 |
| | EMPA111 Blood | 1.4 | 2.2 | 1.9 | 1.9 | 2.8 | 2.9 | 3.2 | 2.7 |
| Grass | 062KC Rubbed in grass | 2.3 | 2.5 | 1.9 | 1.5 | 4.2 | 3.3 | 2.6 | 3.2 |
| | C-H039 Squeezed Grass | 0.4 | 0.3 | 0.0 | 0.0 | 0.2 | 0.3 | 0.8 | 0.5 |
| | CS-08 Grass Extract | 0.2 | 0.0 | −0.1 | −0.1 | 0.4 | 0.1 | 0.2 | 0.2 |
| | PCS-8 Grass Extract | 0.3 | 0.3 | 0.7 | 0.2 | 0.9 | 0.5 | 0.5 | 0.7 |
| | EMPA164 Grass | 1.3 | 1.0 | 0.9 | 0.8 | 1.8 | 0.6 | 1.3 | 0.8 |
| | Grass on cotton | 2.7 | 1.8 | 3.1 | 1.8 | 3.7 | 3.1 | 3.0 | 2.4 |
| | NZ grass | 3.6 | 4.5 | 3.6 | 3.4 | 5.5 | 4.1 | 5.0 | 4.0 |
| BMI | C-05 BMI | 3.7 | 3.7 | 4.1 | 3.4 | 7.2 | 6.6 | 6.9 | 5.4 |
| | EMPA 116 BMI (C) | 6.4 | 7.0 | 6.3 | 5.9 | 8.2 | 8.5 | 7.7 | 7.7 |
| | EMPA 117 BMI (P/C) | 9.3 | 9.6 | 9.2 | 8.0 | 12.7 | 12.8 | 13.3 | 11.5 |
| Cocoa | 038KC Choc. Milk | 1.5 | 1.5 | 1.9 | 1.8 | 2.6 | 2.3 | 1.4 | 1.6 |
| | PC-03 Choc. Milk/carbon black | 3.4 | 2.9 | 3.0 | 2.7 | 4.7 | 4.8 | 4.3 | 3.9 |
| Egg | 051 KC Egg | 2.9 | 2.9 | 2.9 | 2.5 | 3.2 | 3.0 | 3.0 | 2.9 |
| | 10N Whole Egg | 4.0 | 4.2 | 4.4 | 4.1 | 5.5 | 5.3 | 5.4 | 5.3 |
| Food stain | KC-H172 Meat pate | 3.8 | 3.0 | 4.2 | 3.6 | 5.1 | 5.1 | 6.3 | 5.4 |
| | French's brown gravy | 1.4 | 1.2 | 1.5 | 0.9 | 1.5 | 1.3 | 1.5 | 1.3 |

TABLE 24

Delta remission value of detergent comprising proteases compared to detergent without
protease at 30° C. in all Arm & Hammer (The enzymes tested were the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E):

Delta (vs blank) Detergent Arm & Hammer

| Enzyme dose % | 0.25% | | | 0.50% | | | 1.00% | | |
|---|---|---|---|---|---|---|---|---|---|
| Enzymes | 1 | 2 | 3 | 1 | 2 | 3 | 1 | 2 | 3 |
| 108KC ACD sheep blood-dbl app | 0.09 | 0.84 | 0.92 | 1.70 | 0.81 | 0.64 | 1.57 | 2.47 | 1.39 |
| Blood, Hard set | 1.74 | 1.12 | 0.82 | 2.42 | 1.50 | 0.86 | 2.57 | 3.34 | 1.45 |
| Blood, Soft set (Cotton/Polyester) | 5.18 | 3.54 | 3.78 | 6.79 | 7.91 | 6.99 | 6.96 | 1.01 | 3.04 |
| CS-01 Aged blood | 0.84 | 0.20 | −0.18 | 0.25 | 0.20 | −0.14 | 2.16 | −0.03 | 0.38 |
| EMPA111 Blood | 0.27 | 0.60 | −0.16 | 0.74 | 0.88 | 0.24 | 2.05 | 1.35 | 1.21 |
| 062KC Rubbed in grass | 1.03 | 2.81 | 0.40 | 1.23 | −0.18 | 1.08 | 2.94 | 2.73 | 0.24 |
| 062PE Rubbed in grass | 2.45 | 1.14 | 0.64 | 1.62 | 2.88 | 1.88 | 2.25 | 1.75 | 0.53 |
| C-H039 Squeezed Grass | 0.78 | 1.35 | 0.65 | 0.32 | 1.01 | 1.29 | 0.91 | 0.92 | 0.25 |
| CS-08 Grass Extract | 0.11 | 0.16 | 0.49 | 0.31 | 0.23 | 0.37 | 0.20 | 0.18 | 0.15 |
| EMPA164 Grass | 0.27 | 0.24 | 0.11 | 0.65 | −0.28 | 0.20 | 0.55 | 0.85 | −0.18 |
| Grass, cotton | 0.52 | 0.73 | 0.12 | 0.94 | 0.89 | 0.35 | 0.99 | 1.25 | 0.75 |
| NZ Grass CN Grass | 2.12 | 1.33 | 0.31 | 1.91 | 1.50 | 1.31 | 2.41 | 2.88 | 1.31 |
| PCS-8 Grass Extract | 0.34 | 0.03 | 0.27 | 0.58 | 0.39 | 0.13 | 0.59 | 0.32 | 0.40 |
| C-05 BMI | 0.96 | 1.47 | −0.78 | 0.79 | 0.97 | 0.29 | 2.83 | 2.53 | 1.85 |
| EMPA 116 BMI © | 3.54 | 2.67 | 1.93 | 5.35 | 4.24 | 3.45 | 6.71 | 6.27 | 4.81 |
| EMPA 117 BMI (P/C) | 5.03 | 4.31 | 3.95 | 8.11 | 6.62 | 6.10 | 9.96 | 8.48 | 6.74 |
| 038KC Choc. Milk | 2.69 | 2.43 | 2.94 | 3.36 | 2.24 | 4.28 | 3.22 | 3.43 | 3.70 |
| PC-03 Choc. Milk/carbon black | 1.77 | 2.04 | 1.26 | 2.66 | 2.28 | 1.67 | 3.79 | 3.13 | 2.57 |
| 051 KC Egg | 0.96 | 0.84 | 0.63 | 2.08 | 1.38 | 1.10 | 2.54 | 2.32 | 2.28 |
| W10N Whole Egg | 2.05 | 2.31 | 2.12 | 3.23 | 3.25 | 3.11 | 4.14 | 3.71 | 3.62 |
| French's brown gravy (contains wheat protein, beef extract) | 0.83 | 0.87 | 0.79 | 0.86 | 0.90 | 0.65 | 0.97 | 1.06 | 0.80 |
| KC-H172 Meat pate | 3.48 | 3.46 | 3.43 | 4.23 | 4.36 | 3.64 | 5.65 | 5.66 | 3.85 |

TABLE 25

Delta remission value of detergent comprising proteases compared to
detergent without protease at 30° C. in Purex (The enzymes tested were the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E):

Purex

| Enzyme dose % | 0.25% | | | 0.50% | | | 1.00% | | |
|---|---|---|---|---|---|---|---|---|---|
| Enzymes | 1 | 2 | 3 | 1 | 2 | 3 | 1 | 2 | 3 |
| 108KC ACD sheep blood-dbl app | 0.55 | 0.42 | 0.51 | 1.55 | 1.33 | 0.68 | 1.79 | 1.36 | 1.42 |
| Blood, Hard set | 0.51 | 0.17 | 0.30 | 0.77 | 0.45 | 0.39 | 1.50 | 0.99 | 0.56 |
| Blood, Soft set (Cotton/Polyester) | −2.95 | −1.96 | −2.89 | 3.62 | 5.20 | −2.08 | 6.98 | 5.58 | −1.45 |
| CS-01 Aged blood | 0.54 | −0.58 | −0.30 | 1.02 | −0.08 | −0.39 | 1.96 | 1.84 | 0.48 |
| EMPA111 Blood | 0.11 | 0.43 | 0.26 | 0.51 | 1.00 | −0.62 | 1.16 | 1.07 | 1.37 |
| 062KC Rubbed in grass | 1.82 | 1.77 | 2.05 | 1.77 | 1.37 | 1.04 | 1.78 | 2.22 | 1.73 |
| 062PE Rubbed in grass | 3.31 | 3.69 | 2.40 | 4.40 | 3.25 | 3.66 | 5.56 | 5.31 | 3.98 |
| C-H039 Squeezed Grass | −0.44 | 0.81 | 0.09 | 0.48 | 0.29 | 0.06 | 0.40 | 0.89 | −0.09 |
| CS-08 Grass Extract | −0.55 | −0.15 | −0.28 | −0.14 | −0.05 | −0.16 | −0.13 | −0.89 | −0.10 |
| EMPA164 Grass | 1.16 | 0.98 | 0.75 | 1.24 | 1.44 | 0.98 | 1.12 | 1.48 | 0.66 |
| Grass, cotton | 0.91 | 1.18 | 1.39 | 1.37 | 1.34 | 1.08 | 2.18 | 2.22 | 1.67 |
| NZ Grass CN Grass | 1.61 | 1.85 | 1.68 | 2.77 | 2.12 | 1.19 | 3.55 | 3.32 | 1.86 |
| PCS-8 Grass Extract | 0.67 | 0.60 | 0.47 | 1.07 | 0.46 | 0.21 | 0.82 | 0.58 | 0.49 |
| C-05 BMI | 0.65 | −0.33 | 0.37 | 2.33 | 1.44 | 0.12 | 3.94 | 2.38 | 2.32 |
| EMPA 116 BMI © | 3.02 | 3.10 | 3.46 | 5.10 | 5.12 | 3.19 | 7.53 | 6.87 | 4.95 |
| EMPA 117 BMI (P/C) | 3.75 | 4.98 | 4.87 | 6.94 | 5.97 | 5.60 | 9.59 | 8.81 | 8.43 |
| 038KC Choc. Milk | −0.22 | −0.12 | 1.93 | 1.23 | 1.64 | 1.21 | 1.59 | 1.92 | 1.07 |
| PC-03 Choc. Milk/carbon black | 0.98 | 1.17 | 1.26 | 2.20 | 2.07 | 1.46 | 3.75 | 3.34 | 2.47 |
| 051KC Egg | 0.74 | 0.33 | 0.59 | 1.78 | 1.17 | 1.04 | 2.29 | 2.27 | 1.99 |
| W10N Whole Egg | 1.91 | 1.85 | 1.97 | 2.88 | 2.65 | 2.33 | 3.81 | 3.48 | 3.33 |
| French's brown gravy (contains wheat protein, beef extract) | 0.70 | 0.52 | 0.14 | 0.87 | 0.64 | 0.44 | 0.82 | 0.62 | 0.73 |
| KC-H172 Meat pate | 2.80 | 3.27 | 3.31 | 4.16 | 4.56 | 4.52 | 5.37 | 6.30 | 5.41 |

TABLE 26

Delta remission value of detergent comprising proteases compared to detergent without protease at 30° C. in Sun Triple Clean (The enzymes tested were the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E):

Delta (vs blank) Detergent Sun Triple Clean

| Enzyme dose % | 0.25% | | | 0.50% | | | 1.00% | | |
|---|---|---|---|---|---|---|---|---|---|
| Enzymes | 1 | 2 | 3 | 1 | 2 | 3 | 1 | 2 | 3 |
| 108KC ACD sheep blood-dbl app | 1.94 | 1.03 | 0.20 | 1.67 | 2.12 | 1.57 | 2.19 | 2.65 | 1.54 |
| Blood, Hard set | −0.43 | −0.73 | −1.39 | 0.06 | −0.20 | −0.83 | 0.63 | −0.11 | −0.65 |
| Blood, Soft set (Cotton/Polyester) | 2.48 | 0.77 | 0.29 | 2.65 | 3.21 | 2.79 | 5.52 | 2.33 | 2.16 |
| CS-01 Aged blood | −0.02 | −0.11 | −0.52 | 0.92 | 0.28 | −0.29 | 0.88 | 1.55 | 0.03 |
| EMPA111Blood | 0.57 | 0.40 | −0.29 | 1.29 | 0.78 | 0.69 | 1.56 | 1.65 | 0.73 |
| 062KC Rubbed in grass | 1.13 | 1.58 | 0.06 | 1.89 | 1.90 | 0.50 | 2.48 | 2.61 | 1.12 |
| 062PE Rubbed in grass | 2.43 | 1.78 | 1.58 | 2.29 | 2.46 | 1.74 | 3.37 | 2.61 | 1.36 |
| C-H039 Squeezed Grass | 1.19 | 1.76 | 1.36 | 1.17 | 1.24 | 1.39 | 1.64 | 1.78 | 1.07 |
| CS-08 Grass Extract | 0.11 | −0.19 | −0.33 | −0.14 | −0.15 | −0.13 | 0.25 | 0.37 | 0.00 |
| EMPA164 Grass | 0.17 | 0.28 | 0.07 | 0.50 | 0.13 | 0.18 | −0.11 | 0.33 | 0.27 |
| Grass, cotton | 0.85 | 0.89 | 0.79 | 1.26 | 1.63 | 0.81 | 1.83 | 1.58 | 1.36 |
| NZ Grass CN Grass | 1.32 | 1.25 | 0.85 | 2.55 | 1.72 | 1.38 | 2.91 | 2.93 | 1.64 |
| PCS-8 Grass Extract | 0.06 | −0.04 | −0.10 | 0.20 | −0.08 | −0.01 | 0.11 | −0.05 | −0.10 |
| C-05 BMI | 1.48 | 0.62 | 1.18 | 2.30 | 2.42 | 1.41 | 4.07 | 3.26 | 2.22 |
| EMPA 116 BMI © | 4.09 | 3.18 | 2.96 | 5.89 | 4.27 | 3.85 | 6.78 | 6.05 | 5.24 |
| EMPA 117 BMI (P/C) | 4.03 | 3.97 | 3.68 | 6.41 | 6.35 | 5.28 | 8.96 | 8.25 | 5.95 |
| 038KC Choc. Milk | 2.48 | 0.83 | 1.55 | 2.24 | 2.01 | 3.11 | 2.63 | 3.20 | 2.68 |
| PC-03 Choc. Milk/carbon black | 1.63 | 1.40 | 1.28 | 2.18 | 2.08 | 1.88 | 3.77 | 3.29 | 2.36 |
| 051KC Egg | 0.35 | 0.12 | 0.20 | 1.14 | 0.95 | 0.66 | 2.14 | 2.27 | 1.75 |
| W10N Whole Egg | 1.41 | 1.31 | 1.24 | 2.25 | 2.16 | 2.04 | 3.07 | 1.20 | 2.55 |
| French's brown gravy (contains wheat protein, beef extract) | 0.72 | 0.72 | 0.54 | 0.93 | 0.63 | 0.73 | 1.00 | 0.90 | 0.82 |
| KC-H172 Meat pate | 2.72 | 2.62 | 1.68 | 3.04 | 3.95 | 3.03 | 4.18 | 4.69 | 4.91 |

TABLE 27

Delta remission value of detergent comprising proteases compared to detergent without protease at 30° C. in Xtra. The enzymes tested included the following:
1: S9E+N43R+N76D+V205I+Q206L+Y209W+S259D+N261W+L262E;
2: S9E+N43R+N76D+H120V+Q182E+A194P+V205I+Q206L+Y209W+S256D+N261W+L262E+*275aH+*275bH;
3: S3V+N76D+H120V+Q182E+N185E+S188E+V205I+Q206L+Y209W+S216V+S256D+N261W+L262E:

Delta (vs blank) Detergent Xtra

| Enzyme dose % | 0.25% | | | 0.50% | | | 1.00% | | |
|---|---|---|---|---|---|---|---|---|---|
| Enzymes | 1 | 2 | 3 | 1 | 2 | 3 | 1 | 2 | 3 |
| 108KC ACD sheep blood-dbl app | 1.56 | 1.16 | 0.96 | 2.34 | 2.07 | 1.48 | 2.74 | 3.03 | 2.29 |
| Blood, Hard set | 0.34 | 0.24 | −0.31 | 0.97 | 0.08 | −0.13 | 1.31 | 1.40 | 0.35 |
| Blood, Soft set (Cotton/Polyester) | 5.55 | 3.96 | 4.28 | 6.05 | 3.89 | 0.93 | 5.47 | 4.80 | 2.77 |
| CS-01 Aged blood | 0.32 | 0.71 | 0.66 | 1.96 | 1.66 | 1.04 | 2.82 | 2.25 | 1.88 |
| EMPA111 Blood | 0.78 | 0.46 | 0.42 | 1.53 | 1.50 | 1.17 | 1.78 | 2.51 | 1.73 |
| 062KC Rubbed in grass | 0.00 | 1.03 | 1.30 | 2.00 | 1.29 | 0.85 | 1.86 | 2.81 | 1.59 |
| 062PE Rubbed in grass | 2.74 | 2.39 | 2.46 | 5.43 | 2.10 | 2.41 | 2.83 | 5.13 | 3.53 |
| C-H039 Squeezed Grass | 0.49 | 0.08 | 0.80 | 0.60 | 0.00 | 0.74 | 1.23 | 1.34 | 0.38 |
| CS-08 Grass Extract | 0.13 | 0.24 | −0.12 | 0.35 | 0.11 | −0.49 | 0.30 | 0.38 | 0.73 |
| EMPA164 Grass | 0.37 | 0.51 | 0.08 | 0.82 | 0.50 | −0.16 | 0.71 | 1.08 | 0.44 |
| Grass, cotton | 1.40 | 1.11 | 0.06 | 1.74 | 1.03 | 0.63 | 1.44 | 1.97 | 1.03 |
| NZ Grass CN Grass | 1.43 | 1.43 | 1.05 | 2.42 | 1.61 | 1.22 | 3.24 | 3.19 | 2.25 |
| PCS-8 Grass Extract | 1.06 | 0.99 | 0.64 | 0.81 | 0.66 | −0.11 | 0.90 | 0.98 | 0.73 |
| C-05 BMI | 1.58 | 0.92 | 0.93 | 2.32 | 1.65 | 0.35 | 3.00 | 2.31 | 1.98 |
| EMPA 116 BMI © | 3.33 | 3.12 | 2.10 | 4.86 | 4.55 | 3.62 | 6.97 | 7.02 | 5.47 |
| EMPA 117 BMI (P/C) | 4.04 | 3.94 | 3.37 | 7.11 | 5.29 | 4.31 | 8.36 | 8.75 | 6.84 |
| 038KC Choc. Milk | 0.91 | 1.09 | 1.64 | 2.85 | 1.50 | 1.89 | 2.89 | 2.72 | 2.10 |
| PC-03 Choc. Milk/carbon black | 1.73 | 1.26 | 1.10 | 2.45 | 1.81 | 1.47 | 3.19 | 3.75 | 2.89 |
| 051KC Egg | 0.91 | 0.59 | 0.45 | 1.90 | 1.37 | 1.03 | 2.49 | 2.89 | 2.32 |
| W10N Whole Egg | 2.42 | 2.16 | 2.09 | 3.22 | 2.98 | 2.78 | 4.00 | 3.79 | 3.82 |
| French's brown gravy (contains wheat protein, beef extract) | 0.98 | 0.97 | 0.68 | 0.97 | 0.73 | 0.58 | 1.12 | 1.08 | 0.93 |
| KC-H172 Meat pate | 1.12 | 2.20 | 0.83 | 3.75 | 3.18 | 2.40 | 3.96 | 4.68 | 4.16 |

Example 5: Test of Subtilisin 309 Variants in Mini Wash

The wash performance of the proteases of the invention was tested using laundry liquid detergent on one technical stain using the mini wash system.

The Mini wash assay is a test method where soiled textile is continuously lifted up and down into the test solution and subsequently rinsed.

TABLE 28

The wash experiment is conducted under the experimental conditions specified below:

| | |
|---|---|
| Detergent | Tixan-YPE commercial available detergent |
| Detergent dose | 2 g/l |
| pH | As is (i.e. not adjusted) |
| Water hardness | 8.4° dH. |
| Enzyme conc. | Example 20-40-80 nM |
| Test solution volume | 50 ml |
| Test material | EMPA117 EH Blood/milk/ink on cotton/polyester extra heated |
| Temperature | 25° C. |
| Wash time | 20 min soak + 18 min main wash |
| Rinse time | 10 min |
| Test system | Soiled textile continuously lifted up and down into the test solutions, 50 times per minute (up-time 0.29 sec, down-time 0.29 sec, lift time 0.17 sec). The test solutions are kept in 125 ml glass beakers. After wash of the textiles are continuously lifted up and down into tap water, 50 times per minute (up-time 0.5 sec, down-time 5 sec, lift time 0.5 sec). |

Test materials were obtained from EMPA Testmaterials AG Movenstrasse 12, CH-9015 St. Gallen, Switzerland.

The textiles were subsequently air-dried and the wash performance was measured as the brightness of the color of these textiles. Brightness can also be expressed as the Remission (R), which is a measure for the light reflected or emitted from the test material when illuminated with white light. The Remission (R) of the textiles was measured at 460 nm using a Zeiss MCS 521 VIS spectrophotometer. The measurements were done according to the manufacturer's protocol.

Calculating the enzyme effect was done by taking the measurements from washed swatches with enzymes and subtract with the measurements from washed without enzyme for each stain, $\Delta \text{Rem}_{enzyme}$.

The experiments were conducted as described in the mini wash assay for laundry method with the detergent composition and swatches under the experimental conditions as specified in Table 29 below.

TABLE 29

Experimental conditions for mini wash laundry experiments

| | |
|---|---|
| Detergent dosage | YPE, 2 g/L |
| Test solution volume | 50 mL |
| pH | As is |
| Wash time | 20 min soak + 18 min main wash |
| Temperature | 25° C. |
| Water hardness | 8.4° dH |
| Protease concentration | 0-20-40-80 nM |
| Swatch | EMPA 117 EH |

Water hardness was adjusted to 8.4° dH by addition of $CaCl_2$, $MgCl_2$, and $NaHCO_3$ ($Ca^{2+}:Mg^{2+}:CO_3=2:1:4.5$) to the test system. After washing the textiles were rinsed in tap water and dried.

TABLE 30

Relative performance of proteases subtilisin 309 variants compared to detergent with Subtilisin 309 (SEQ ID NO: 2) at 25° C.

| Enzyme | 20 nM | 40 nM | 80 nM |
|---|---|---|---|
| Subtilisin 309 (SEQ ID NO: 2) | 1.0 | 1.0 | 1.0 |
| S9E + N43R + N76D + A158E + A194P + N204D + V205I + Q206L + Y209W + S212G + S215V + L262E | 1.1 | 1.3 | 1.1 |
| S9E + N43R + N76D + A158E + G160P + V205I + Q206L + Y209W + S259D + N261W + L262E | 1.1 | 1.5 | 1.5 |
| S9E + N43R + N76D + A158E + G160P + A194P + N204D + V205I + Q206L + Y209W + S212G + S216V + L262E | 1.1 | 1.2 | 1.3 |
| S9E + N43R + N76D + A158E + G160P + S161E + A194P + N204D + V205I + Q206L + Y209W + S216V + L262E + *275aH + *275bH | 0.9 | 1.1 | 1.1 |
| S9E + N43R + N76D + A158E + G160P + S161E + A194P + N204D + V205I + Q206L + Y209W + L262E | 0.8 | 1.0 | 1.1 |
| S9E + N43R + N76D + A158E + G160P + S161E + A194P + N204D + V205I + Q206L + Y209W + S212G + S216V + L262E + *275aH + *275bH | 0.8 | 0.9 | 1.3 |
| S9E + N43R + N76D + A158E + G160P + S161E + A194P + N204D + V205I + Q206L + Y209W + S212G + L262E | 1.0 | 1.2 | 1.4 |
| S9E + N43R + N76D + A158E + A194P + V205I + Q206L + Y209W + S259D + N261W + L262E | 0.9 | 1.3 | 1.5 |
| S9E + N43R + N76D + A158E + G160P + S161E + A194P + N204D + V205I + Q206L + Y209W + S212G + L262E + *275aH + *275bH | 0.7 | 0.9 | 1.0 |
| S9E + N43R + N76D + A158E + G160P + S161E + A194P + N204D + V205I + Q206L + Y209W + S216V + L262E | 1.1 | 1.2 | 1.3 |
| S9E + N43R + N76D + A158E + G160P + S161E + A194P + Q206L + Y209W + S259D + L262E + *275aH + *275bH | 0.9 | 0.8 | 1.1 |
| S9E + N43R + N76D + A158E + G160P + S161E + A194P + V205I + Q206L + Y209W + S212G + S216V + L262E | 1.2 | 1.2 | 1.3 |
| S9E + N43R + N76D + A158E + S161E + V205I + Q206L + Y209W + S259D + N261W + L262E | 0.8 | 1.2 | 1.4 |
| S9E + N43R + N76D + A158E + G160P + S161E + V205I + Q206L + Y209W + S259D + N261W + L262E | 0.7 | 1.1 | 1.1 |

TABLE 30-continued

Relative performance of proteases subtilisin 309 variants compared to detergent with Subtilisin 309 (SEQ ID NO: 2) at 25° C.

| Enzyme | 20 nM | 40 nM | 80 nM |
|---|---|---|---|
| S9E + N43R + N76D + A158E + S161E + A194P + N204D + V205I + Q206L + Y209W + S212G + S216V + L262E | 1.0 | 1.2 | 1.1 |
| S9E + N43R + N76D + G160P + V205I + Q206L + Y209W + S259D + N261W + L262E | 1.1 | 1.3 | 1.3 |
| S9E + N43R + N76D + A194P + N204D + V205I + Q206L + Y209W + S212G + S216V + S259D + N261W + L262E | 1.1 | 1.1 | 1.1 |
| S9E + N43R + N76D + A194P + Q206L + Y209W + L262E | 1.1 | 1.1 | 1.1 |
| S9E + N43R + N76D + A194P + Q206L + Y209W + S256D + S259D + N261W + L262E | 0.9 | 0.9 | 1.0 |
| S9E + N43R + N76D + A194P + Q206L + Y209W + T255E + S256D + S259D + T260E + N261W + L262E | 1.1 | 1.1 | 1.2 |
| S9E + N43R + N76D + V205I + Q206L + Y209W + S259D + N261W + L262E | 1.1 | 1.3 | 1.2 |
| S9E + N43R + N76D + G115W + H120V + A194P + Q206L + Y209W + S259D + L262E | 0.9 | 1.0 | 1.1 |
| S9E + N43R + N76D + G115W + H120V + P129D + A194P + Q206L + Y209W + S259D + L262E | 0.8 | 1.0 | 0.9 |
| S9E + N43R + N76D + G160P + A194P + N204D + V205I + Q206L + Y209W + S212G + S216V + L262E | 1.3 | 1.4 | 1.2 |
| S9E + N43R + N76D + G160P + S161E + A194P + N204D + V205I + Q206L + Y209W + S212G + S216V + L262E | 1.1 | 1.4 | 1.3 |
| S9E + N43R + N76D + G160P + S161E + A194P + N204D + V205I + Q206L + Y209W + S212G + S216V + L262E + *275aH + *275bH | 1.4 | 1.5 | 1.5 |
| S9E + N43R + N76D + N204D + V205I + Q206L + Y209W + S259D + N261W + L262E | 1.0 | 1.1 | 1.4 |
| S9E + N43R + N76D + G160P + S161E + V205I + Q206L + Y209W + S259D + N261W + L262E | 1.1 | 1.2 | 1.3 |
| S9E + N43R + N76D + H120V + Q182E + A194P + V205I + Q206L + Y209W + S256D + N261W + L262E + *275aH + *275bH | 1.0 | 1.1 | 1.1 |
| S9E + N43R + N76D + V205I + Q206L + Y209W + S216V + S259D + N261W + L262E | 0.8 | 1.0 | 1.2 |
| S9E + N43R + N76D + S161E + V205I + Q206L + Y209W + S259D + N261W + L262E | 0.9 | 1.0 | 1.5 |
| S9E + N43R + N76D + P131* + A194P + Q206L + Y209W + S259D + L262E | 1.5 | 1.4 | 1.4 |
| S9E + N43R + N76D + H120V + Q182E + A194P + V205I + Q206L + Y209W + S256D + N261W + L262E + *275aH + *275bH | 0.9 | 1.0 | 1.2 |
| S9E + N43R + N76D + S161E + A194P + N204D + V205I + Q206L + Y209W + S212G + S216V + L262E + *275aH + *275bH | 0.9 | 1.2 | 1.2 |
| S9E + N43R + N76D + V205I + Q206L + Y209W + S212G + S259D + N261W + L262E | 1.0 | 1.2 | 1.5 |
| S9E + N43R + N76D + N204D + V205I + Q206L + Y209W + S212G + S216V + S259D + N261W + L262E | 1.1 | 1.2 | 1.3 |

The results Table 30 show that the Subtilisin309 variants showed improved or on par wash performance compared to Subtilisin309 (SEQ ID NO: 2) on Blood/milk/ink at 25° C.

The invention claimed is:

1. A liquid cleaning composition having pH from about 7 to about 13 comprising a protease, wherein the protease is a protease variant having at least 60% identity to the amino acid sequence of SEQ ID NO:1 or 2, and wherein said variant comprises substitutions at positions 205, 209, and one or more additional substitutions at 218 or 259, corresponding to positions of SEQ ID NO:1.

2. The liquid cleaning composition of claim 1, wherein the composition has a pH from about 8 to about 13.

3. The liquid cleaning composition of claim 1, wherein the composition has a pH from about 9 to about 13.

4. The liquid cleaning composition of claim 1, wherein the composition has a pH from about 10 to about 13.

5. The liquid cleaning composition of claim 1, wherein the composition has a pH from about 11 to about 13.

6. The liquid cleaning composition of claim 1, wherein the protease variant comprises substitutions at positions 205, 209, 218 and 259.

7. The liquid cleaning composition of claim 1, wherein the variant comprises substitution X205G, X205A, X205L, X205M, X205F, X205W, X205K, X205Q, X205E, X205S, X205P, X205C, X205Y, X205H, X205R, X205N, X205D, or X205T.

8. The liquid cleaning composition of claim 1, wherein the variant comprises substitution X209G, X209A, X209M, X209F, X209W, X209K, X209Q, X209E, X209S, X209P, X209V, X209I, X209C, X209H, X209R, X209N, X209D, or X209T.

9. The liquid cleaning composition of claim 1, wherein the variant comprises substitution X218G, X218A, X218L, X218M, X218F, X218W, X218K, X218Q, X218E, X218S, X218P, X218V, X218I, X218C, X218Y, X218H, X218R, X218D, or X218T.

10. The liquid cleaning composition of claim 1, wherein the variant comprises substitution X259G, X259A, X259L, X259M, X259F, X259W, X259K, X259Q, X259E, X259P, X259V, X259I, X259C, X259Y, X259H, X259R, X259N, or X259T.

11. The liquid cleaning composition of claim 1, wherein the variant has an amino acid sequence which has at least 65% sequence identity to the amino acid sequence of SED ID NO:1 or 2.

12. The liquid cleaning composition of claim 1, wherein the parent protease is SEQ ID NO:1 or SEQ ID NO:2.

13. The liquid cleaning composition of claim 1, which comprises one or more additional enzymes selected from the group comprising of perhydrolases, amylases, catalases, cellulases, cutinases, haloperoxygenases, lipases, mannanases, pectinases, pectin lyases, peroxidases, proteases, DNases, xanthanases, and xyloglucanases, or any mixture thereof.

14. A liquid cleaning composition comprising:
    (a) from 0% to 20% wt of a detergent surfactant;
    (b) from 40% to 95% wt water;
    (c) from 1% to 30% wt of an alkaline buffer system comprising an alkali metal silicate or an alkali metal hydroxide or a mixture thereof, to provide a pH of from about 11 to 13.5; and
    (d) from 0.001% to 10% wt of a protease variant, wherein the protease variant is a variant of a parent protease, wherein the protease variant has an amino acid sequence which has at least 60% identity to the amino acid sequence of SEQ ID NO:1 or 2, and wherein said variant comprises substitutions at positions 205, 209, and one or more additional substitutions at 218 or 259, corresponding to positions of SEQ ID NO:1.

15. A liquid cleaning composition comprising:
    (a) from 0% to 20% wt of a detergent surfactant;
    (b) from 0.001% to 10% of a protease variant, wherein the protease variant a variant of a parent protease, wherein said protease variant has an amino acid sequence which has at least 60% identity to the amino acid sequence of SEQ ID NO:1 or 2, and wherein said variant comprises substitutions at positions 205, 209, and one or more additional substitutions at 218 or 259, corresponding to positions of SEQ ID NO:1; and
    (c1) from 20% to 95% wt water; or
    (c2) from 1% to 30% wt of an alkaline buffer system comprising an alkali metal silicate or an alkali metal hydroxide or a mixture thereof, to provide a pH of from about 8 to 13.5.

16. A liquid cleaning composition comprising: at least 0.01 wt % protease, wherein the protease is a variant of a parent protease and the protease has an amino acid sequence which has at least 60% sequence identity to the amino acid sequence of SEQ ID NO: 1 or 2, and wherein said protease variant is characterized by having at least 10% higher residual activity than the parent protease when measured after 4 hours at 40° C. in liquid detergent with pH 10, and wherein said variant comprises substitutions at positions 205, 209, and one or more additional substitutions at 218 or 259, corresponding to positions of SEQ ID NO:1.

17. A liquid cleaning composition comprising:
   (a) from 20% to 95% wt water; and
   (b) at least 0.01 wt % protease, wherein the protease is a variant of a parent protease and the protease has an amino acid sequence which has at least 60% sequence identity to the amino acid sequence of SEQ ID NO: 1 or 2, and wherein said protease variant is characterized by having at least 10% higher residual activity than the parent protease when measured after 4 hours at 40° C. in liquid detergent with pH 10, and wherein said variant comprises substitutions at positions 205, 209, and one or more additional substitutions at 218 or 259, corresponding to positions of SEQ ID NO:1.

18. A liquid cleaning composition comprising:
   (a) from 0% to 20% wt of a detergent surfactant;
   (b) from 0.001% to 10% wt of a protease variant, wherein the protease variant is a variant of a parent protease and the protease variant has an amino acid sequence which has at least 60% sequence identity to the amino acid sequence of SEQ ID NO: 1 or 2, and wherein said variant comprises substitutions at positions 205, 209, and one or more additional substitutions at 218 or 259, corresponding to positions of SEQ ID NO:1; and
   (c1) from 20% to 95% wt water; or
   (c2) from 1% to 30% wt of an alkaline buffer system comprising an alkali metal silicate or an alkali metal hydroxide or a mixture thereof, to provide a pH of from about 11 to 13.5.

19. The liquid cleaning composition of claim 1, wherein the variant has an amino acid sequence which has at least 70% sequence identity to the amino acid sequence of SED ID NO:1 or 2.

20. The liquid cleaning composition of claim 1, wherein the variant has an amino acid sequence which has at least 80% sequence identity to the amino acid sequence of SED ID NO:1 or 2.

\* \* \* \* \*

```
                        SEQUENCE LISTING

<160> NUMBER OF SEQ ID NOS: 2

<210> SEQ ID NO 1
<211> LENGTH: 275
<212> TYPE: PRT
<213> ORGANISM: Bacillus amyloliquefaciens

<400> SEQUENCE: 1

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
```

```
                35                  40                  45
Ser Met Val Pro Ser Glu Thr Asn Pro Phe Gln Asp Asn Asn Ser His
 50                  55                  60

Gly Thr His Val Ala Gly Thr Val Ala Ala Leu Asn Asn Ser Ile Gly
 65                  70                  75                  80

Val Leu Gly Val Ala Pro Ser Ala Ser Leu Tyr Ala Val Lys Val Leu
                 85                  90                  95

Gly Ala Asp Gly Ser Gly Gln Tyr Ser Trp Ile Ile Asn Gly Ile Glu
             100                 105                 110

Trp Ala Ile Ala Asn Asn Met Asp Val Ile Asn Met Ser Leu Gly Gly
         115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 2
<211> LENGTH: 269
<212> TYPE: PRT
<213> ORGANISM: Bacillus lentus

<400> SEQUENCE: 2

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
         50                  55                  60

His Val Ala Gly Thr Ile Ala Ala Leu Asn Asn Ser Ile Gly Val Leu
 65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
             100                 105                 110

Gly Asn Asn Gly Met His Val Ala Asn Leu Ser Leu Gly Ser Pro Ser
         115                 120                 125
```

-continued

```
Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145             150                 155                     160

Tyr Pro Ala Arg Tyr Ala Asn Ala Met Ala Val Gly Ala Thr Asp Gln
            165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```